US009700614B2

(12) United States Patent
Arwidsson et al.

(10) Patent No.: US 9,700,614 B2
(45) Date of Patent: Jul. 11, 2017

(54) INTRANASAL VACCINATION DOSAGE REGIMEN

(71) Applicant: Eurocine Vaccines AB, Solna (SE)

(72) Inventors: Hans Arwidsson, Strängnäs (SE); Anna-Karin Maltais, Spånga (SE)

(73) Assignee: Eurocine Vaccines AB, Solna (SE)

( * ) Notice: Subject to any disclaimer, the term of this patent is extended or adjusted under 35 U.S.C. 154(b) by 0 days.

(21) Appl. No.: 14/650,831

(22) PCT Filed: Dec. 17, 2013

(86) PCT No.: PCT/EP2013/076905
§ 371 (c)(1),
(2) Date: Jun. 9, 2015

(87) PCT Pub. No.: WO2014/095866
PCT Pub. Date: Jun. 26, 2014

(65) Prior Publication Data
US 2016/0184424 A1   Jun. 30, 2016

(30) Foreign Application Priority Data

Dec. 17, 2012   (DK) ................................ 2012 70788

(51) Int. Cl.
| *A61K 39/145* | (2006.01) |
| *A61K 39/12* | (2006.01) |
| *A61K 39/39* | (2006.01) |
| *A61K 39/00* | (2006.01) |

(52) U.S. Cl.
CPC ............ *A61K 39/145* (2013.01); *A61K 39/12* (2013.01); *A61K 39/39* (2013.01); *A61K 2039/5252* (2013.01); *A61K 2039/54* (2013.01); *A61K 2039/543* (2013.01); *A61K 2039/545* (2013.01); *A61K 2039/55511* (2013.01); *A61K 2039/55566* (2013.01); *C12N 2760/16134* (2013.01); *C12N 2760/16234* (2013.01)

(58) Field of Classification Search
None
See application file for complete search history.

(56) References Cited

FOREIGN PATENT DOCUMENTS

| WO | WO 02/080648 A2 | 10/2002 |
| WO | WO 2006/125076 A2 | 11/2006 |
| WO | WO 2012/042003 A1 | 4/2012 |

OTHER PUBLICATIONS

Barchfeld et al. (Vaccine. 1999; 17: 695-704).*
Petersson et al. (Vaccine. 2010; 28: 6491-6497).*
Falkeborn et al. (PLOSOne. Aug. 2013; 8 (8): e70527).*
Ambrose, Christopher S. et al., "The safety and effectiveness of self-administration of intranasal live attenuated influenza vaccine in adults" Vaccine, 2013, pp. 857-860, vol. 31.
Falkeborn, Tina et al., "Endocine™, N3OA and N3OASq; Three Mucosal Adjuvants That Enhance the Immune Response to Nasal Influenza Vaccination" PLOS ONE, Aug. 2013, pp. 1-9, vol. 8, Issue 8, e70527, XP009172690.
Haile, M. et al., "Immunization with heat-killed *Mycobacterium bovis* bacille Calmette-Guerin (BCG) in Eurocine™ L3 adjuvant protects against tuberculosis" Vaccine, 2004, pp. 1498-1508, vol. 22.
Joseph, Aviva et al., "A new intranasal influenza vaccine based on a novel polycationic lipid-ceramide carbamoyl-spermine (CCS) I. Immunogenicty and efficacy studies in mice" Vaccine, 2006, pp. 3990-4006, vol. 24.
Kendall, Mark "Vaccinating against influenza in children without needles: A new initiative" Journal of Pediatric Infectious Diseases, 2012, pp. 83-88, vol. 7.
Nichol, Kristin et al., "Effectiveness of Live, Attenuated Intranasal Influenza Virus Vaccine in Healthy, Working Adults" JAMA, Jul. 14, 1999, pp. 137-144, vol. 281, No. 2.
Nichol, Kristin L. "Live attenuated influenza virus vaccines: new options for the prevention of influenza" Vaccine, 2001, pp. 4373-4377, vol. 19.
International Search Report for PCT/EP2013/076905 dated Apr. 2, 2014.

* cited by examiner

*Primary Examiner* — Shanon A Foley
(74) *Attorney, Agent, or Firm* — Knobbe Martens Olson & Bear LLP

(57) ABSTRACT

The present invention relates in a first aspect to a vaccine kit comprising a) a first vaccine component comprising i) a first set of one or more containers, each container containing a vaccine composition for intranasal administration, b) optionally a second vaccine component comprising a second set of one or more containers, each container containing a vaccine composition for intranasal administration, and c) optionally instructions for use, wherein each container of the first and second set of containers contains a volume of the vaccine composition from about 5 microliter to about 400 microliter. The present invention also relates to: An administration regimen for intranasal administration of a vaccine composition for use in immunizing a human. A device for use in administration of vaccine compositions. The use of: a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter for immunizing a human. The use of: a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter for the preparation of a vaccine for intranasally immunizing a human. The method of treating a person in need of a vaccination. The vaccine formulated for intranasal administering.

Figure 1:
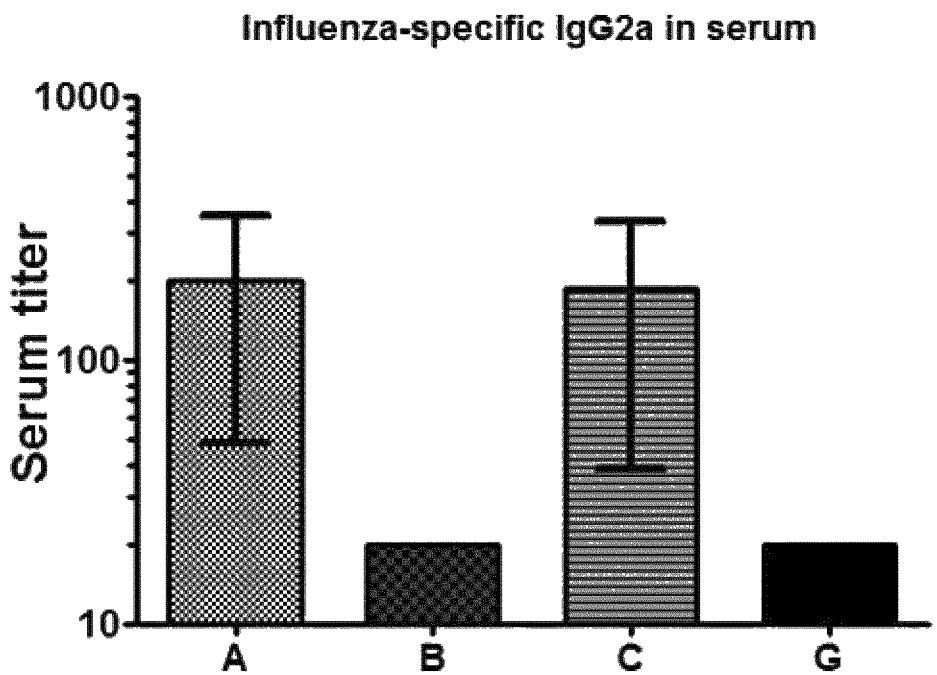

13 Claims, 2 Drawing Sheets

INTRANASAL VACCINATION DOSAGE REGIMEN

CROSS REFERENCE TO RELATED APPLICATIONS

This application is a U.S. National Phase Application of PCT International Application Number PCT/EP2013/076905, filed on Dec. 17, 2013, designating the United States of America and published in the English language, which is an International Application of and claims the benefit of priority to Danish Patent Application No. PA 2012 70788, filed on Dec. 17, 2012. The disclosures of the above-referenced applications are hereby expressly incorporated by reference in their entireties.

FIELD OF THE INVENTION

The present invention enables a novel administration regimen for administration of vaccines for use in immunizing a human. It allows for vaccinations without administration of the vaccine by medically trained personnel.

BACKGROUND OF THE INVENTION

Most vaccine compositions are administered parenterally via injection. In recent years, other delivery routes for vaccines have been studied such as administration via mucosal surfaces in the nose or in the oral cavity. It is known that for most types of vaccines, a better immunization is achieved by administering the vaccine more than one time, e.g. as a prime dose and one or more boost doses, where the boost dose(s) is later in time than the prime dose.

Very often, the prime dose—and also one or more boost doses—is given parenterally by injection using a needle and a syringe. Only medically trained people are permitted to administer a vaccine composition parenterally. The fact that the patients need to go to a clinic for administration of a vaccine by medically trained people dissuades and refrains some from achieving e.g. one or more boost doses. Poor patient compliance subsequently leads to insufficient or less sufficient immunization. Thus, there is a need to improve present vaccination regimens in order to enable improved compliance and immunization.

Furthermore, situations might also occur where there is a need for fast immunization of large masses of people and where it is beneficial for people to avoid hospital settings with other potentially contagious people. Such a situation might include an influenza pandemic or a similar situation where a virus spreads quickly and there is an urgency to immunize many persons. In such a situation it would be valuable with a vaccine composition in a form that enables self-administration without any need of medically educated or trained personnel. The present invention allows for self-administration of a vaccine.

The present invention provides a kit that enables an improved compliance for immunization. The kit contains vaccine composition in a form that enables self-administration without any need of medically educated or trained personnel. Thus, a person can vaccinate herself or—in the case of children or disabled persons—with help from another not-medically trained person (e.g a parent or caretaker).

US 2011/200635 relates to a method for preparing vaccines that can raise immunity against both seasonal and pandemic strains. The vaccines can be administered in single dose or multiple doses. In a multiple dose schedule the various doses may be given by the same or different routes. Self-administration is not anticipated by US 2011/200635.

WO 2012/024283 describes a universal flu vaccine that gives protection against various strains of influenza. Multiple doses of a vaccine can be employed. Self-administration is not anticipated by WO 2012/024283.

US 2010/0150954 relates to specific immunogenic conjugates. Self-administration is not anticipated by US 2010/0150954.

EP 2,396,030 corresponding to WO 2010/092476 describes a method comprising administering to the human a first vaccine comprising antigen from a pandemic-associated influenza virus strain; and then week(s) (1, 2, 6) later, administering to the same human a second influenza vaccine comprising antigen from the pandemic-associated influenza virus strain. The most preferred immunization route is by intramuscular injection (e.g. into the arm or leg). Self-administration is not anticipated by EP 2,396,030 or WO 2010/092476.

US 2010/0143393 describes influenza antigen formulations and vaccines. Multiple dosage regimens are described, but self-administration is not anticipated.

US 2007/0224220 relates to a composition of influenza virosomes. Single administration to a human is described to be sufficient for the induction of a systemic immune response. Self-administration is not anticipated by US 2007/0224220.

Rudenko et al. (2001) disclose a study of elderly where the immunogenicity and efficacy of Russian live attenuated (intranasal live attenuated influenza vaccine) and US inactivated trivalent (intra muscular inactivated influenza vaccine) influenza vaccines administered alone or in three different combinations were evaluated. Postvaccination serum antibody responses were more frequent among individuals administered the combination vaccines than among those vaccinated with live or inactivated vaccine alone. Only individuals who received live vaccine, alone or in combination with inactivated vaccine, achieved significant post-vaccination increases in virus-specific nasal IgA. Self-administration is not anticipated by Rudenko et al.

SUMMARY OF THE INVENTION

The present invention relates in a first aspect to a vaccine kit comprising
 a) a first vaccine component comprising i) a first set of one or more containers, each container containing a vaccine composition for intranasal administration,
 b) optionally a second vaccine component comprising a second set of one or more containers, each container containing a vaccine composition for intranasal administration, and
 c) optionally instructions for use,
 wherein each container of the first and second set of containers contains a volume of the vaccine composition from about 5 microliter to about 400 microliter.

The invention further provides a vaccine kit comprising
 a) a first vaccine component comprising i) a first set of one or more containers, wherein one of the containers contains a vaccine composition for intranasal administration, and wherein another or the same container contains an adjuvant,
 b) optionally a second vaccine component comprising a second set of one or more containers, wherein one of the containers contains a vaccine composition for intranasal administration, and wherein another or same container contains an adjuvant, and
 c) optionally instructions for use,
 wherein each container of the first and second set of containers comprising the vaccine compositions contains a volume of the vaccine composition from about 5 microliter to about 400 microliter.

In one embodiment, the vaccine kit of the invention is for use in situations where there is a need for fast immunization of large masses of people or where it is beneficial for people to avoid hospital settings with other potentially contagious people. Alternatively stated, the vaccine kit may be for use in an influenza pandemic or a similar situation where a virus spreads quickly and there is an urgency to immunize many persons. The vaccine kit of the invention is typically for use in self-administration without any need of medically educated or trained personnel, such as but not limited to in the event of an influenza pandemic or a similar situation where a virus spreads quickly and there is an urgency to immunize many persons. The present invention is directed to the use for self-administration of a vaccine.

The present invention provides a kit that enables an improved compliance for immunization. The kit contains vaccine composition in a form that enables self-administration without any need of medically educated or trained personnel. Thus, a person can vaccinate him or herself or—in the case of children or disabled persons—with help from another not-medically trained person (e.g. a parent or care-taker).

FIGURES

Figure 2:
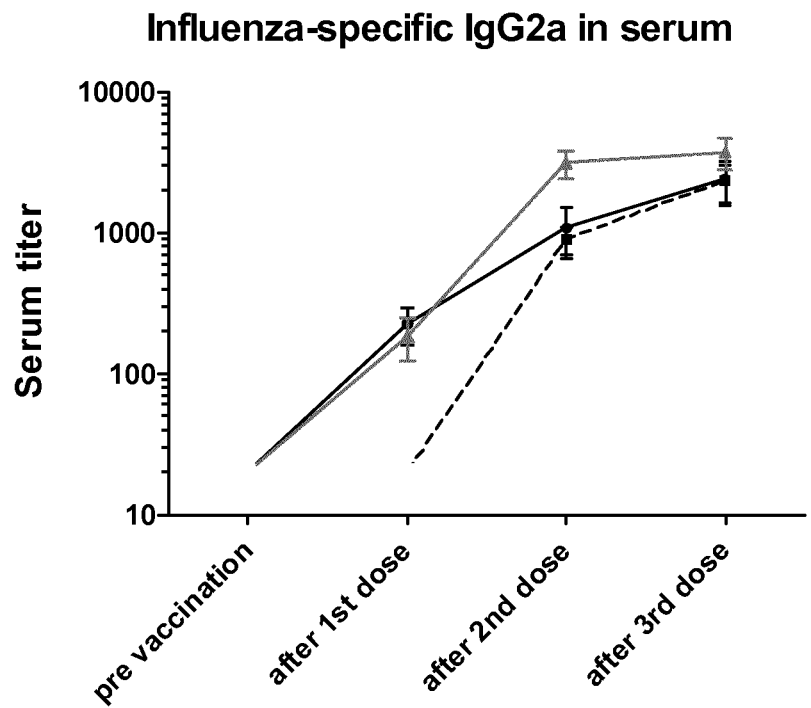
Figure 3:
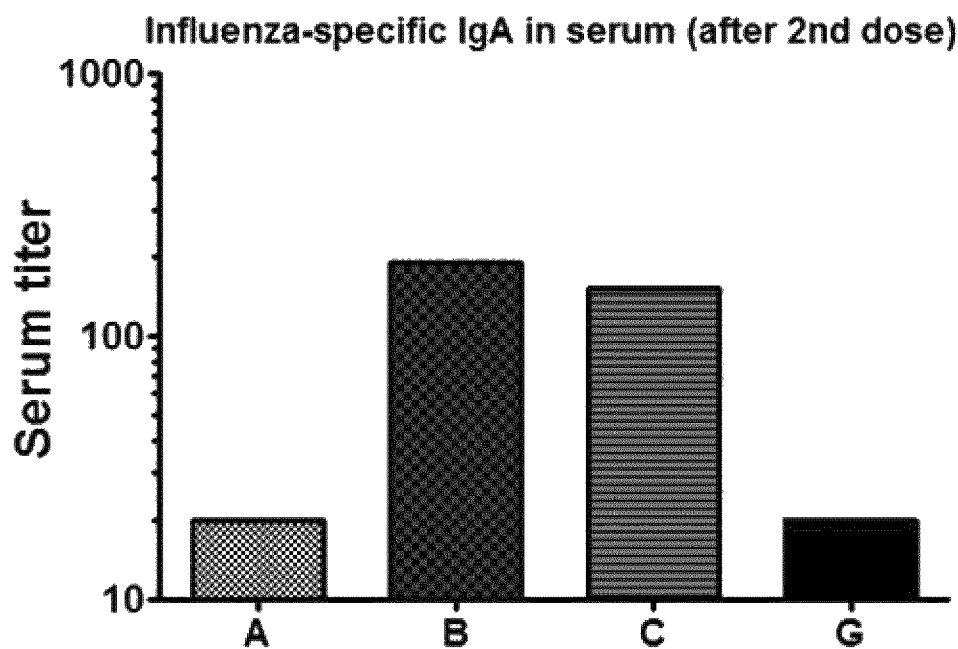
Figure 4:
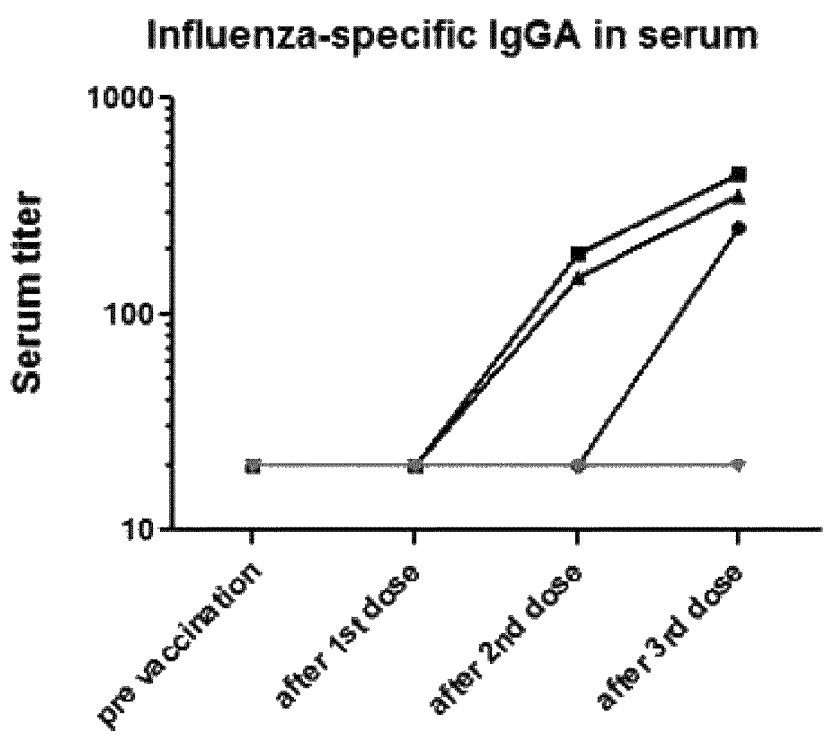

FIG. 1 shows influenza-specific IgG2a in serum day 21 (after prime). Group B had lower serum IgG2a titers compared to the groups that got a parenteral injection at prime (group A and C). Mean (95% CI) is shown (n=8).
- A. 1.5 ug s.c. prime
- B. 1.5 ug i.n. prime
- C. 1.5 ug sc+1.5 ug in prime
- G. Saline in FIG. 2 shows influenza-specific IgG2a in serum. Mean and error (SEM) is shown. No significant differences could be seen in group A-C after the third dose, however after the first dose group B showed significantly lower serum IgG2a titers compared to the groups that got a parenteral injection at prime (group A and C).
- A. 1.5 ug s.c. prime
- B. 1.5 ug i.n. prime
- C. 1.5 ug sc+1.5 ug in prime
- G. Saline in FIG. 3 shows influenza-specific IgA in serum. Median IgA titers after $2^{nd}$ dose is shown (day 42).
- A. 1.5 ug s.c. prime
- B. 1.5 ug i.n. prime
- C. 1.5 ug sc+1.5 ug in prime
- G. Saline in FIG. 4 shows influenza-specific IgA in serum. Median IgA titers are shown.
- A. 1.5 ug s.c. prime
- B. 1.5 ug i.n. prime
- C. 1.5 ug sc+1.5 ug in prime
- G. Saline in

DESCRIPTION OF THE INVENTION

The invention provides a vaccine kit comprising
a) a first vaccine component comprising i) a first set of one or more containers, each container containing a vaccine composition for intranasal administration,
b) optionally a second vaccine component comprising a second set of one or more containers, each container containing a vaccine composition for intranasal administration, and
c) optionally instructions for use,
wherein each container of the first and second set of containers contains a total volume of the vaccine composition from about 5 microliter to about 400 microliter.

In a further aspect, the present invention provides a vaccine kit comprising
a) a first vaccine component comprising i) a first set of one or more containers, wherein one of the containers contains a vaccine composition for intranasal administration, and wherein another or the same container contains an adjuvant,
b) optionally a second vaccine component comprising a second set of one or more containers, wherein one of the containers contains a vaccine composition for intranasal administration, and wherein another or the same container contains an adjuvant, and
c) optionally instructions for use,
wherein each container of the first and second set of containers comprising the vaccine compositions contains a total volume of the vaccine composition from about 5 microliter to about 400 microliter.

In one embodiment, this aspect of the invention is particularly suited when the vaccine compositions to be administered are unstable. By having the adjuvant separated from the vaccine composition before administration, a more stable medical package can be ensured. The adjuvant and the vaccine composition can then be mixed just before use of the respectively first and/or second vaccine component.

In the present context, the term "set of containers" is intended to denote a number of containers, where the number is in a range of from 1 to 10. Thus, a set of containers may be one container, it may be two containers, it may be three containers etc.

The term "vaccine" is defined herein as a composition, suspension or solution of antigenic moieties, usually consisting of inactivated infectious agents or inactivated whole viruses or bacteria, or some parts thereof, that is introduced to a human body to produce active immunity.

In the present context, the term "vaccine composition for intranasal administration" is intended to mean that the composition is designed for intranasal self-administration. Moreover, as it also appears from the following, the volume of the composition to be administered is important and must be relatively low in order to make sure that the composition is applied correctly to the nasal mucosa. The composition may contain one or more additives, which are acceptable for use in the nose. It is important that the vaccine composition for intranasal administration is provided in a form that makes it possible to administer the composition by self-administration.

The term "self-administration" means that the composition can be administered to the nose by the patient herself and the patient does not need to be medically trained. When it is a child or a disabled person who is subject to vaccination, the administration may be exerted by another person. However, also in this case, the person does not need to have any medical training in order to administer the vaccine composition correctly to the nose.

The term "adjuvant" as used herein is any substance or combinations of substances which in admixture with an immunogen increases or otherwise modifies the immune response by immune stimulation or by increased and/or improved antigen delivery.

The term "antigen" or "immunogen" is defined as anything that can serve as a target for an immune response. The term also includes protein antigens, recombinant protein components as well as genetically engineered RNA or DNA, which—when injected into the cells of the body—the "inner machinery" of the host cells "reads" the DNA and uses it to synthesize the pathogen's proteins. Because these proteins are recognised as foreign, when they are processed by the host cells and displayed on their surface, the immune system is alerted, which then triggers a range of immune responses. The term also includes material, which mimic inactivated bacteria or viruses or parts thereof. The immune response can be either cellular or humoral and be detected in systemic and/or mucosal compartments.

The term "parenterally administered" refers to administration by the parenteral route, e.g. intramuscular, intravenous, intradermal, or subcutaneous administration.

The term "dose" or "intranasally administered dose" refers to the amount of antigen or antigens (e.g. inactivated virus or bacterium) to be delivered or delivered to the nasal mucosa. The dose is normally administered such that approximately 50% of the dose is administered to each nostril. The "volume of vaccine" is the volume of the composition in which the dose (amount of antigen) is present. It is therefore the total volume of the composition to be administered for one full dose. The volume of the vaccine is the volume of administration for a dose.

Thus, if the composition besides the antigen(s) comprises e.g. an adjuvant, a solvent, a dispersion medium, additives etc. it is the "volume of the vaccine" composition administered. The volume of the vaccine composition should be divided equally over the mucosa of the two nostrils, 50% of the volume to one nostril and the remaining 50% to the other nostril.

The total volume contained in a container may correspond to the total volume of the vaccine composition for administration of one dose that is needed to be administered instranasally. However, for practical purposes, it may be preferable to have a well-defined volume reside in the container after administration. This extra volume results in that the total volume of the container is slightly greater that the in the volume of the vaccine composition. A person skilled in the art will know how to determine the correct total volume in the container.

However, in some embodiments, the volume of the container corresponds to about half the volume of the vaccine for one dose or half the total volume. That is to say that volume of the container may be the amount to be administered to one nostril in addition to the extra volume in the container. Otherwise stated, the dose or total dose of the antigen(s) contained in a container may be the total dose to be applied, or it may be divided into more containers such as e.g. 50% of the dose, such as in two containers. In this situation, the content of two containers is administered each containing 50% of the dose or total dose, normally one to each nostril.

In some embodiments, the vaccine regimen may comprise the intranasal administration of more than one vaccine composition with more than one antigen in more than one adjuvant. Accordingly, in such embodiments the term "total dose" relates to the total amount of antigens, each antigen having a defined dose. The term "total volume of vaccine" refers to the total volume of one vaccine composition or the volume of each of its component containers (e.g the sum of the volume of the adjuvant containing composition in one container with the volume of the antigen containing composition in another container).

As stated, the vaccine composition of the invention contains a total volume of the vaccine composition from about 5 microliter to about 400 microliter. In some embodiments, a vaccine composition of the invention with a total volume of, for example 200 microliter would be divided between two containers with 2×100 microliters in each container. Alternatively, the invention is also directed to a kit of parts comprising one vaccine composition (e.g. Vaccine A) in two containers of, for example 2×100 microliters in each container and a second vaccine (e.g. Vaccine B) in two containers of, for example, 2×150 microliters. The total volume for each vaccine is less than 400 microliters but the total volume of vaccines in the kit may be more than 400 microliters.

The total dose is the total dose to be administered intranasally. As stated, in either a prime dose or booster dose, it may be necessary to couple the intranasal administration with a parenteral administration. Accordingly, this overall dose is the combined dose of the intranasal dose and the parenteral dose.

The term "dosage unit" means the container or containers for intranasal administration of the total dose comprising the intranasal vaccine composition and the one or more containers. It optionally further comprises any device for intranasal administration.

The vaccine composition is in liquid form such as in the form of a solution, an emulsion, dispersion or a suspension.

As mentioned above, the volume of the vaccine composition is important. The volume of the vaccine composition contained in a container of the first or second set of containers must be relatively small such as at the most 400 μl. Normally, the volume is from about 5 μl to about 400 from about 15 μl to about 300 μl, from about 30 μl to about 250 μl, from about 50 μl to 200 μl, or from about 50 μl to 150 μl such as 100 μl. The volume may also be from about 30 μl to about 150 μl such as 100 μl, e.g. in those cases where a child is subject to vaccination. The volume may also depend on the type and potency of the antigens contained in the vaccine composition.

This small volume is important in order to ensure convenience for the patient when the dose is administered and to avoid entrance of the composition into the throat or lungs, where the vaccine does not exert its effect. Moreover, if a larger volume is applied there is a risk that the composition may float out of the nostrils after application. A suitable small size of the composition is also important for improving patient compliance.

Any combination of the volume ranges mentioned above for the vaccine compositions is within the context of the present application. Moreover, the broadest range mentioned gives a preferred range, and then the range is narrowed to the most preferred range.

A container of the first and second set of containers may be in the form of a pipette or spray, or a suitably formed plastic container that easily can be opened by the patient and where its content is easily delivered to the mucosa of the nose.

The first vaccine component may also contain one or more vaccine compositions for parenteral administration. If this is the case medically trained personnel is required to administer this composition. The composition for parenteral administration may be a known composition such as e.g. a composition which is available on the market or has a potential thereto. However, the present invention focus on how to enable a better patient compliance, which will lead to a better immunization and, which in turn, will lead to a less need for hospitalization of patients and, accordingly, have positive effect on the social costs. This is achieved by providing vaccine compositions for intranasal administration in a suitable small volume.

The specific combination of e.g. parenteral/intranasal administration as a prime dose and intranasal administration of one or more boost doses will depend on the vaccination in question.

A prime dose consisting only of an intranasal administered vaccine composition may give sufficient immune response and then it is not necessary to strengthen the immune response by including a parenterally administered vaccine composition in the prime dose. In such situations, no medically trained personnel are required to administer the vaccine composition as it can easily be self-administered, but the intranasal administration can also be administered by or under supervision of medically trained personnel.

In other cases the intranasal administered vaccine composition may not be sufficient as a prime dose to obtain a sufficient immune response. In such cases it may be necessary to stimulate the immune response by a parenterally administered vaccine composition preferably given as a part of a prime dose.

Accordingly, embodiments of the invention comprise vaccination protocols where the prime dose or the booster dose or both is administered in whole or in part intranasally, and in part or not parenterally. Similarly, embodiments of the invention comprise vaccination protocols where the prime dose or the booster dose or both is administered in whole or in part intranasally by self-administration, and in part by medically trained personnel.

In those cases where the type of vaccination requires a prime and one or more boost doses, both the first and the second component of the kit may be present. The first component contains the means for the prime dose and the second component contains the means for one or more boost doses.

As mentioned above, the means for the prime dose may be a set of containers, wherein each container contains a composition for intranasal administration. The means for the prime dose may also be a set of containers, wherein each container contains a composition for intranasal administration, in combination with a vaccine composition for parenteral administration.

The means for one or more boost doses is a set of containers, wherein each container contains a composition for intranasal administration.

The vaccine compositions contain one or more antigens. The antigen(s) contained in the individual vaccine compositions may be the same or different. Moreover, the antigen(s) may be effective against the same disease or type of disease, or the antigens may be effective against two or more diseases.

The kit of the invention may be designed so that the antigens vary depending on circulating bacterium or virus strains (e.g. influenza). The kit of the invention may also be designed so that the antigens are constant over time.

Preferably the antigen(s) in the vaccine compositions in the first and second set of containers are as defined herein. They may be inactivated bacteria or viruses or parts thereof in order to improve the safety aspects. This is in contrast to what is on the market. Today intranasal compositions with live attenuated vaccines are approved for humans and available on the market. However, use of live vaccines represents a safety risk. Thus, if the containers and equipment used are not destroyed properly it poses potential occupational and environmental health risks.

Moreover, there is a risk of virus transmission from a person vaccinated with a vaccine containing live virus to another person. In a large phase III trial LAIV (live attenuated vaccine), compared with TIV (inactivated vaccine) was associated with an increased incidence of medically significant wheezing in vaccine-naive children aged <24 months and with an increased incidence of hospitalization in children aged 6-11 months. Thus, there is also a need for more safe vaccines. The present invention provides intranasal compositions preferably comprising inactivated viruses or bacteria or parts thereof.

As mentioned above, LAIV vaccines require special disposing of vaccines since it is alive biological material. Thus, such risk must be taken into account before self-administration can be a reality. As the vaccine compositions for intranasal administration of the present invention does not contain alive material as the antigens are inactivated, the waste does not have the safety risk associated with LAIV and essential has no safety risk associated with storage and disposal. Thus, the present approach enables self-administration.

The antigens may be e.g. whole inactivated antigens such as e.g. whole inactivated viruses. The antigen may also be part of a pathogen such as e.g. part of an inactivated virus. The antigen components that may be used are, but not limited to, for example, viral, bacterial, mycobacterial or parasitic antigens as indicated below. Bacterial pathogens for use according to the invention are indicated below.

The dose of the antigen(s) will depend on which antigen that is used and is within the knowledge of a person skilled in the art. In the table below is given some specific examples.

Doses of Examples of Viral or Bacterial Antigens

| Virus/Bacteria | Brand namn | Dose | Conjugate |
|---|---|---|---|
| Meningococci | Menveo | A: 10 ug, conj. 16.7-33.3 ug<br>C: 5 ug, conj. 7.1-12.5 ug<br>W: 5 ug, conj. 3.3-8.3 ug<br>Y: 5 ug, conj. 5.6-10 ug | CRM197 |
|  | Neis-Vac C | C: 10 ug, conj. 10-20 | Tetanustoxoid |
|  | Menactra | A, C, W, Y: 4 ug, conj. 48 ug | Diphteria toxoid |
| Herpes zoster |  |  |  |
| HPV | Gardasil | Type 6, 18: 20 ug<br>Type 11, 16: 40 ug |  |
|  | Cervarix | Type 16, 18: 20 ug |  |
| Rotavirus | Rotateq |  |  |
|  | Rotarix |  |  |
| RSV | Novavax Phase I trial | Protein F: 5, 15 or 30 ug |  |

-continued

| Virus/Bacteria | Brand namn | Dose | Conjugate |
|---|---|---|---|
| HIB | Pentavac/Infanrix | 10 ug | |
| Pertussis | Pentavac/Infanrix | 25 ug | |
| Polio | Pentavac/Infanrix | Type 1, D antigen: 40 E | |
| | | Type 2, D antigen: 8 E | |
| | | Type 3, D antigen: 32 E | |
| Tetanus | Pentavac/Infanrix | >40 IE | |
| Diphteria | Pentavac/Infanrix | >30 IE | |
| Hepatitis A | Twinrix | 360 ELISA-units | |
| Hepatitis B | Twinrix | 10 ug | |
| Seasonal | Fluarix | A: 15 ug (per subtype) | |
| Influenza | | B: 15 ug (per subtype) | |
| | Fluzone High-Dose | A: 60 ug (per subtype) | |
| | | B: 60 ug (per subtype) | |
| | Intanza | A: 9 ug (per subtype) | |
| | | B: 9 ug (per subtype) | |
| Pandemic influenza | Pandemrix | A: 3.75 ug | |

The one or more antigens contained in the vaccine compositions for intranasal administration may be:

Antigens Against Viruses:
 i) antigens against Influenza A, Influenza B, RSV, Human metapneumovirus (hMPV), Human papillomavirus (HPV), Rotavirus, Norovirus, HIV, Herpes simplex, and/or Parainfluenza virus (OIV), or mixtures thereof,
 ii) antigens against Rhino virus, SARS, Coronaviruses, Herpes zoster/varicella, Hepatitis A-E, Hantavirus, and/or Cytomegalovirus, or mixtures thereof, Antigens Against Bacteria:
 i) antigens against Pneumococci and/or Meningococci, or mixtures thereof,
 ii) antigens against *Haemophilus influenzae* b, *Bacillus anthracis, Chlamydia trachomatis, Pseudomonas aeruginosa, Mycobacterium tuberculosis*, Diphtheria, *Escherichia coli.* Group *Streptococcus, Neisseria gonorrhoeae* and/or *Bordetella pertussis* or mixtures thereof, or Other Antigens:
 i) antigens against diphtheria, tentanus, pertussis, polio, measles, mumps, rubella, cervixal cancer and/or chickenpox, or mixtures thereof,
 or
 mixtures thereof.

Antigens Against Allergies:
 i) antigens inducing an immune response against allergies due to house dust mite, pollen and other environmental allergens, food, insect bite, latex, cosmetic, animals and/or nickel or mixtures thereof.

Any combination of the antigens mentioned above is within the context of the present application.

In some situations it may be of importance to achieve an immunological response in the nasal mucosa. By using the intranasal route of administration, the immunization happens in the mucosa which makes the present administration regimen relevant for all diseases that are being transported into our bodies via mucosal membranes (many viruses and bacteria are air-borne via droplets and transmitted via the air-ways to the persons).

Thus, the antigens present in a vaccine composition for intranasal administration may also be against diseases including or caused by:

Diseases Related to Virus Group 1:
Influenza A,
Influenza B,
Respiratory syncytial virus (RSV),
Human metapneumovirus (hMPV),
Human papillomavirus (HPV),
Rotavirus,
Norovirus,
Human immunodeficiency virus (HIV),
Herpes simplex,
Parainfluenza virus (OIV), Diseases Related to Virus Group 2:
Rhino virus,
Severe acute respiratory syndrome (SARS),
Coronaviruses,
Herpes zoster/varicella,
Hepatitis A-E,
Hantavirus,
Cytomegalovirus, Diseases Related to Bacteria Group 1:
Pneumococci,
Meningococci, Diseases Related to Bacteria Group 2:
*Haemophilus influenzae* b (Hib)
*Bacillus anthracis,*
*Chlamydia trachomatis,*
*Pseudomonas aeruginosa,*
*Mycobacterium tuberculosis,*
Diphtheria,
*Escherichia coli.*
Group *Streptococcus,*
*Neisseria gonorrhoeae,*
*Bordetella pertussis.*

Within each virus or bacterium mentioned herein, antigens against different strains may be used.

All the antigens mentioned above may also be included in the vaccine composition for parenteral administration if it is part of the first vaccine component of the kit according to the invention.

Each container of the first and/or second set of containers may contain the same or different antigen(s), or it may contain the same or different mixture of antigens.

In a preferred aspect, each container of the first and/or second set of containers contains the same or same mixture of antigens. Preferably, the concentration of antigens in each container is the same. Moreover, each container of the second set of containers preferably contains the same or same mixture of antigens. Preferably, the concentration of antigens in each container is the same. It is also preferred that each container of the first and second set of containers contains the same or same mixture of antigens, and in the same concentration.

The vaccine composition may be a multi-vaccine composition containing up to 30 antigens, normally from 2 to 13 different kinds. An example is a multi-vaccine that protects against five distinct diseases: diphtheria, tetanus, pertussis, polio and *Haemophilus influenzae* type b. Such a vaccine is today only available for parenteral administration. With the kit of the invention it is possible to provide many multi-vaccines. Another example is of a multi-antigen vaccine such as Prevenar which protects against pneumococcal disease and today contains up to 13 different pneumococcal antigens. The containers of the first and/or second set of containers may e.g. contain a vaccine composition containing all the antigen(s) (i.e. only one type of composition with respect to antigens), or each container may contain one or some of the antigens, whereas other containers contain the other antigen(s). Thus, this principle makes it possible to combine different vaccine compositions in a flexible manner dependent on which diseases the vaccines should protect against. Moreover, any problems relating e.g. to stability, solubility etc., which may be seen in compositions containing multi-antigens may be reduced when the antigens are present in separate containers. However, in general one container contains all antigens in a multi-vaccine composition.

Other antigens that could be of interest in a multi-vaccine are antigens that protect against: influenza A, influenza B, tetanus, pertussis, polio, Haemophilus influenza type b (hib), meningitis C, Pneumococcal infection, measles, mumps, rubella, cerivcal cancer, hepatitis B, tuberculosis (TB), chickenpox, norovirus and other diseases.

Antigens against allergies that could be of interest in a multi-vaccine are antigens inducing an immune response against allergies due to house dust mite, pollen and other environmental allergens, food, insect bite, latex, cosmetic, animals, and/or nickel or mixtures thereof Also antigens against seasonal allergies such as spring, summer, fall could be of interest in a multi-vaccine. For instance, some trees such as oak, elm, and maple pollinate in the spring, while grasses such as Bermuda, timothy and orchard pollinate in the summer Plant pollens could be ryegrass, timothy-grass, ragweed, plantego, nettle, birch, alder, hazel, hornbeam willow, poplar, platanus, tilia, olea, ashe juniper among others.

Animal allergies could be cat, dog, rabbit due to fur and dander.

Food allergies could be against all kind of nuts, eggs, legumes, fruit, corn, milk, seafood, soy, wheat.

In the field of vaccines, there are many different forms of vaccines known in the art and these vaccines can be administered to patients according to different regimen e.g. multiple dosage vaccination.

Currently, many vaccines are given as a prime followed by one or more booster doses of vaccination. However, the booster dose(s) are not always administered on schedule or at all. But if a simple means of administering the booster dose was available it is envisaged that the booster dose would be given more often and would improve the immunological response to the vaccine. Accordingly, in one embodiment, the present invention relates to a booster dose for a vaccine regimen. Alternatively, the vaccine regimen may be entirely comprised in the vaccination kit of the invention. Furthermore, one embodiment of the invention relates to a vaccine kit for the pediatric vaccination regimens or parts thereof. The vaccination kit of the invention is typically suitably formulated for nasal administration to children and to any person.

Moreover, compliance could be improved and thereby better protection against disease induced. The elderly (50+ years) would strongly benefit from induction of stronger immune response, but multiple parenteral vaccinations are not always considered feasible in the elderly. Nasal boosters could enable multiple vaccinations in the elderly and therefore lead to improved compliance, improved immune responses and better protection against disease. Accordingly, one embodiment of the invention relates to a vaccine kit for the elderly or for geriatric patients. The vaccination kit of the invention is typically suitably formulated for nasal administration to the elderly or geriatric patients and to any person.

The inventors have shown that in humans vaccinated nasally with an influenza vaccine containing the adjuvant Endocine™ there is an influenza-specific mucosal (nasal) immune response generated (nasal IgA antibodies). In patients vaccinated parenterally with an influenza vaccine there are much lower titers of influenza-specific antibodies in the nasal mucosa. Nasal vaccination can provide a mucosal immune response (nasal IgA) that is not generated (or generated only at low levels) by parenteral vaccination. Combining parenteral and nasal vaccination at the same time point may generate a broader immune response compared to vaccinating parenterally alone, or the parenteral administration may be completely substituted with intranasal administration to obtain a sufficient immune response.

Accordingly, one embodiment of the invention relates to a vaccination regimen combining parenteral and nasal vaccination, at the same time point or separated in time.

In some subjects, it is difficult to evoke a sufficient immune response and in such cases a boost dose should be given. This is often the case in children (younger than 8 years) and in the elderly (>50 years), but it is envisaged that many other people would benefit from a boost dose and a stronger and repetitive stimulation of the immune system. However, up to now compositions have not been provided in a form that enables self-administration and, accordingly, only persons of low age or with naïve immune systems (such as in case of pandemic) have been offered a boost dose against influenza. The present vaccination kit is not limited to a class of patients or subjects but is expected to be of particular utility in children and infants under 8 years old and in the elderly (>50 years) and geriatric patients.

In some cases the intranasally administered prime dose of vaccine gives sufficient immune response and it is not necessary to strengthen the immune response by a parenterally administered dose. Accordingly, in one embodiment of the invention, the vaccination kit is for administration of the prime dose of vaccine or vaccines. In such situations, no medically trained personnel is required to administer the dose as it can easily be self-administered.

In other cases e.g. for persons with not yet fully developed immune systems (children below the age of 5 and even more so below the age of 2) or vaccine antigen naïve immune systems (common in children 0-8 years) or persons with immune systems at least partly affected by immunosenescence (older adults and elderly age 50+), the intranasally administered dose of vaccine may not be sufficient to obtain a sufficient immune response. In such cases, an embodiment of the invention is directed to stimulating the immune response by a parenterally administered dose (i.e. the prime dose is a combination of intranasal and parenteral administration).

As explained above, the focus of the present invention is vaccination, where it is an advantage also to obtain specific nasal immune response (as many viruses or bacteria are air-borne and transmitted via the air-ways to the persons).

When such a combined vaccination is required as prime dose, the parenterally administered dose and the intranasally administered dose may be administered by medically educated personnel at the same visit to the medical clinic. This may also be the case in the future, but the provision of a vaccine composition designed for self-administration enables other dosage regimens. Thus, there may be cases where it is advantageous to obtain a nasal immune response as a first response. In such cases the intranasal dose should be administered before the parenterally administered dose. In other situations it may be advantageous to obtain the nasal immune response as a second response. In these cases the intranasal dose should be administered after the parenterally administered dose. However, in both of these situations, the person can administer the intranasal dose by self-administration. In those situations where it is advantageous to administer the two doses at the same point of time, the medically trained personnel may administer both doses, but still the advantage having one or more containers with the metered amount of the vaccine composition for intranasal administration makes it much easier to ensure a correct dosing of the vaccine. Moreover, it is needle-free and enables a better compliance.

Accordingly, the invention comprises embodiments where the vaccine or vaccines of the vaccine kit of the invention is administered intranasally as the prime dose, as the boost dose, as the sole dose, or as both the prime dose or and boost dose or doses. Many variations with respect to prime and boost dose are known from the literature and are encompassed by the present invention.

The vaccine may consist of the antigen(s) alone in a suitable medium such as, e.g., an aqueous medium including water, and/or it may contain further ingredients. Such ingredients include:

1. Adjuvants, which can function to enhance the immune response elicited in a patient who receives the vaccine. Many adjuvants have been suggested in the literature. The Applicant's own adjuvant Endocine™ is generally preferred and has been disclosed in WO 2012/042003, but the invention is not limited to specific adjuvants etc. as the gist of the invention is to provide a vaccine formulated for self-administration. Marketed adjuvants suitable for use in the present invention include:

AS01, AS02, AS03, AS04 from GSK
MF59 from Novartis
CRM197 (used for protein conjugations)
Nanostat from Nanobio
GLA (TLR-4 agonist) from ImmuneDesign/Medimmune
Ampligen from Hemispherex Biopharma
Vaxisome from Nasvax
Matrix-M (a saponin derivative) from Isconova
Iscomatrix (a saponin derivative) from CSL
Proteosome adjuvants from GSK (formerly ID Biomedical)
Nanocarriers from Incellart
QS21 Stimulon from Agenus
IC31 from Intercell
Bacerium-Like Particle (BLP) aka Mimopath technology from Mucosis
E6020 from Eisai
Resequimod from 3M Drug Delivery Systems
DNA adjuvant: Flt3 ligand or CpG oligodeoxunucleotides
W085EC from University of Michigan (Dr. James R Baker)
Invaplex from Walter Reed
AFCo1 from Finlay Institute
Cholera toxin (CT) or heat-labile toxin (LT)-derivatives and mutants.

Other adjuvants may be such as e.g., oils such as squalene or soybean oil or an aluminum salt such as e.g. aluminum hydroxide, aluminum phosphate, aluminum hydroxyphosphate sulfate, aluminum potassium sulfate or any combination thereof Many other adjuvants have been suggested in the literature, see e.g. US 2011/0200635 (Banzhoff et al.), which is incorporated in its entirety by reference.

A suitable adjuvant for intranasal administration may be an adjuvant that comprises a monoester of glycerol optionally in combination with a fatty acid, or it may be a combination of fatty acids. Carboxylic acids used in such adjuvants comprise long chain (C4-C30) alkyl, alkenyl or alkynyl carboxylic acids which may optionally be branched or unbranched, cyclic or acyclic, optionally having single, double or multiple unsaturation (double or triple bond) which may further optionally be of different kind.

Monoglycerides used as such adjuvants may be carboxylic acid esters of glycerin, wherein the carboxylic acids may be long chain (C4-C30) alkyl, alkenyl or alkynyl carboxylic acids which may optionally be branched or unbranched, optionally having single, double or multiple unsaturation (double or triple bond) which may further optionally be of different kind.

The concentration of monoglyceride in a vaccine composition may be in the range of e.g. about 1 to about 50 mg/ml. Typically, the vaccine composition contains a monoester of glycerol with a fatty acid in a concentration of from 5 to 40 mg/ml, such as, e.g. from about 1 to about 25 mg/ml, from about 5 to about 15 mg/ml or about 10 mg/ml.

The concentration of fatty acid in a vaccine composition may be in the range of e.g. about 0.5 to about 50 mg/ml, such as, e.g. from about 1 to about 25 mg/ml, from about 1 to about 15 mg/ml, from about 1 to about 10 mg/ml, from about 2 to about 8 mg/ml or about 6-7 mg/ml. In one embodiment, on a molar basis the concentration of a fatty acid in the vaccine composition corresponds to the concentration (on a molar basis) of the monoglyceride.

Any combination of the concentration ranges mentioned above for monoglyceride and fatty acid is within the context of the present application. Moreover, the broadest range mentioned gives a preferred range, and then the range is narrowed to the most preferred range.

The term "carboxylic acid" encompasses branched or unbranched, cyclic or acyclic, substituted or unsubstituted alkyl, alkenyl and alkynyl carboxylic acids, optionally having single, double or multiple unsaturation (double or triple bond) which may further optionally be of different kind (double and triple bonds in any mix or combination), of from 4 to 30 carbon atoms, such as, e.g., from 6 to 24 carbon atoms, from 8 to 20 carbon atoms or from 12 to 20 carbon atoms. It is also understood that the definition is intended to also cover different types of diastereoisomerism (cis-trans isomers), which may be in any combination. Examples are, but not limited to; lauric acid (C12), myristic acid (C14), palmitic acid (C16), palmitoleic acid (C16:1), oleic acid (C18:1), linoleic acid (C18:2) and stearic acid. Other examples are hexanoic acid, caprylic acid, decanoic acid (capric acid), arachidic acid, behenic acid, lignoceric acid, alpha-linolenic acid, stearidonic acid, eicosapentaenoic acid, docosahexaenoic acid, gamma-linolenic acid, dihomo-gamma-linolenic acid, arachidonic acid, erucic acid and nervonic acid. Encompassed are also combinations thereof The term "monoglyceride" encompasses carboxylic acid mono-esters of glycerine (propane-1,2,3-triol) wherein the carboxylic acid may be branched or unbranched, cyclic or acyclic, substituted or unsubstituted alkyl, alkenyl and alkynyl carboxylic acids, optionally having multiple unsaturation (double or triple bond) which may further optionally be of different kind, of from 4 to 30 carbon atoms, such as, e.g., from 6 to 24 carbon atoms, from 8 to 20 carbon atoms or from 12 to 20 carbon atoms. It is also understood that the definition is intended to also cover different types of diastereoisomerism (cis-trans isomers), which may be in any combination. Encompassed are also combinations thereof.

Examples of acids used in the esterification of glycerol are, but not limited to, lauric acid (C12), myristic acid (C14), palmitic acid (C16), palmitoleic acid (C16:1), oleic acid (C18:1), linoleic acid (C18:2) and stearic acid. Other examples are hexanoic acid, caprylic acid, decanoic acid (capric acid), arachidic acid, behenic acid, lignoceric acid, alpha-linolenic acid, stearidonic acid, eicosapentaenoic acid, docosahexaenoic acid, gamma-linolenic acid, dihomo-gamma-linolenic acid, arachidonic acid, erucic acid and nervonic acid.

The inventors of the present invention have found that adjuvants as described above and disclosed in WO 2012/042003 (which is hereby included in its entirety by reference) are particularly useful when vaccination is performed via the nasal route, e.g. administration to the mucosa of the nasal cavity. The inventors have found that use of such adjuvants in vaccination via the nasal route improves the immune response upon vaccination. The inventors have found the use of such adjuvants safe and tolerable in several species including humans.

The applicant's own adjuvant Endocine™ is in accordance with the above.

Endocine™ composition comprises:

| Substances | CAS number* |
|---|---|
| Glycerol mono-oleate | 97593-29-8 |
| Oleic acid | 112-80-1 |
| Water | — |

The adjuvant is preferably used in vaccines in a 2% lipid concentration in the final vaccine composition when the vaccine is for adults.

The Endocine™ adjuvant is preferably used comprising equimolar amounts of glycerol monooleate and oleic acid with a final concentration of 20 mg/ml in the vaccine composition.

All the above mentioned adjuvants can also be used according to the second aspect of the present invention wherein the adjuvant is placed in a separate container than the vaccine composition or otherwise kept separate from the vaccine until mixing just before use.

2. Agents to Control the Tonicity/Osmolarity of the Vaccine. Such Agents are e.g. Physiological salts like sodium chloride. Other physiological salts are potassium chloride, potassium dihydrogen phosphate, disodium phosphate, magnesium chloride etc. Such agent could also be other ionic substances which influence the ionic strength and stability. The osmolality of the vaccine may be adjusted to a value in a range from about 200 to about 400 mOsm/kg, preferably in a range from about 240 to about 360 mOsm/kg or the osmolality must be close to the physiological level e.g. in the physiological range from about 290 to about 310 mOsm/kg.

3. Agents to adjust the pH of or to buffer the vaccine composition. Normally, pH of the vaccine composition is in a range of from about 5 to about 8.5. Variations in pH of nasal and parenteral vaccine compositions are acceptable. The pH of the nasal mucosa is from 5 to 6.7, and pH of plasma is about 7.4. Suitable pH adjusting agents or buffer substances include hydrochloric acid, sodium hydroxide (to adjust pH) as well as phosphate buffer, Tris buffer, citrate buffer, acetate buffer, histidine buffer etc. (to buffer the vaccine).

4. Other additives like e.g. surface-active agents, antioxidants, chelating agents, antibacterial agents, viral inactivators, preservatives, dyes, anti-foaming agents, stabilizers or surface active agents, or combinations thereof.

The surface-active agent may be hydrophilic, inert and biocompatible, such as, e.g., poloxamers such as e.g. Pluronic F68 or Pluronic 127.

The antibacterial agents may be e.g. amphotericin or any derivative thereof, chlorotetracyclin, formaldehyde or formalin, gentamicin, neomycin, polymyxin B or any derivative thereof, streptomycin or any combination thereof The antioxidants may be e.g. ascorbic acid or tocopherol or any combination thereof The viral inactivators may be e.g. formalin, beta-propiolactone, UV-radiation, heating or any combination thereof.

The preservatives may be e.g. benzethonium chloride, EDTA, phenol, 2-phenoxyethanol or thimerosal or any combination thereof. EDTA has also been shown to be a chelating agent, an antioxidant and a stabilizer.

The dyes may be e.g. any indicators (such as e.g. phenol red) or brilliant green or any combination thereof.

The anti-foaming agents may be e.g. polydimethylsilozone.

The surfactants may be e.g. anionic, cationic or non-ionic or zwitterionic, such as e.g. polyoxyethylene and derivatives thereof, polysorbates (such as e.g. polysorbate 20 or polysorbate 80), Tween 80, poloxamers (such as e.g Pluronic F68) or any combination thereof.

The table below gives examples of different dosage regimes. The term "i.m." refers to intramuscularly, but could also be by other parenteral routes such as subcutaneous or intradermal.

| Regimen | Prime dose | Boost dose(s) | | |
|---|---|---|---|---|
| No. | Dose 1 | Dose 2 | Dose 3 | Dose 4 |
| 1 | i.n | | | |
| 2 | i.n. | i.n | | |
| 3 | i.n. | i.n. | i.n. | |
| 4 | i.n. | i.n. | i.n. | i.n |
| 5 | i.m. | i.n. | | |
| 6 | i.m. and i.n. | i.n. | | |
| 7 | i.m. and i.n. | i.n. | i.n. | |

No. 1 relates to a regimen consisting of a prime dose administered intranasally. The prime dose may be split in more than one container, e.g. in two containers, where the content of each container is adminstered to a nostril.

No. 2 is a regimen identical with No 1, but with one boost dose only given intranasally. Dose 2 is given at a certain time period after Dose 1.

No. 3 is a regimen identical with No. 2, but with a second boost dose is given intranasaly. Dose 3 is given at a certain time period after Dose 2

No. 4 is a regimen identical with No. 3, but with a third boost dose. Dose 4 is given at a certain time period after Dose 3.

No. 5 relates to a regimen where the prime dose is given parenterally and the first boost dose is given intranasally. The boost dose may be split in more than one container, e.g. in two containers, where the content of each container is administered to a nostril. Dose 2 is given at a later point in time than Dose 1. A second or further boost dose may also be administered intranasally.

No. 6 relates to a regimen where the prime dose is given both parenterally and intranasally, and the first boost dose is given intranasally. The dose given intranasally may be split in more than one container, e.g. in two containers, where the content of each container is administered to a nostril.

No. 7 is identical to No. 3, but with a second boost dose intranasally administered (Dose 3). Dose 3 is normally given at a certain time period after Dose 2.

The time interval between the prime and the boost doses and between the individual boost doses depend on the antigens used. If the antigen(s) provides protection against a seasonal disease involving a virus or bacterium that can change from year to year (e.g. influenza), then the interval is at least 3 or 4 weeks, normally not longer than 3-5 weeks. If the antigen(s) provides protection against non-seasonal diseases (involving a virus or bacterium that do not change or change modestly) then the time interval normally is much longer such as months or even years. An example is e.g. that the prime is at age 3 months and that there are 3 following boosters, 2 months, 7 months and 5 years+9 months after the prime dose (i.e. vaccination of a person at age 3, 5, 12 months and 6 years).

The invention is therefore further directed to a kit, wherein the vaccine composition for intranasal administration is given by self-administration, but the intranasal administration can also be administered by or under supervision of medically trained personnel. The kit may comprise a vaccine composition for intranasal administration and for parenteral administration wherein both are administered by or under supervision of medically trained personnel.

In the table below is given the same regimens as in the table above, but with an indication of the nature of the antigen used.

| Regimen No. | Prime dose Dose 1 | Boost dose(s) Dose 2 | Dose 3 | Dose 4 |
|---|---|---|---|---|
| 1 | Inactivated | | | |
| 2 | Inactivated | Inactivated | | |
| 3 | Inactivated | Inactivated | Inactivated | |
| 4 | Inactivated | Inactivated | Inactivated | Inactivated |
| 5 | Inactivated | Inactivated | | |
| 6 | Inactivated | Inactivated | | |
| 7 | Inactivated | Inactivated | Inactivated | |

The antigen(s) may be as defined herein. Thus, it may be an inactivated bacterium or virus or parts thereof. An inactivated virus antigen may be split, subunit or whole virus.

As mentioned herein, and as it appears from the appended claims, many possibilities are present with respect to construction of a kit according to the invention, e.g. with respect to content of antigen(s), the same or different vaccine compositions, combination of routes of administration, time interval between prime and boost dose etc.

Influenza

As mentioned above, the novel regimen may be used in many types of vaccination. Without limiting the invention thereto, in the following influenza vaccination is used as an example.

Today the most effective method for preventing virus infection is to be vaccinated against the virus with a vaccine.

In the field of influenza vaccines, there are many different forms of influenza vaccines known in the art and these influenza vaccines can be administered to patients according to different regimen e.g. single or multiple dosage vaccination. In the following reference is made to some of the known applications in the field of multiple dosage influenza vaccination.

With respect to influenza vaccination, children (with an age of at least 6 months) may get booster doses of influenza vaccination. However, the use of a booster dose varies from country to country, but if a simple means of administering the booster dose was available it is envisaged that the booster dose would be given as well in order to improve the immunological response. Moreover, compliance could be improved and thereby better protection against disease induced. The elderly (50+ years) would strongly benefit from induction of stronger immune response, but multiple parenteral vaccinations against influenza are not considered feasible in the elderly. Nasal boosters could enable multiple vaccinations in elderly and therefore lead to improved compliance, improved immune responses and better protection against influenza disease.

The inventors have shown that in humans vaccinated nasally with an influenza vaccine containing the adjuvant Endocine™ there is an influenza-specific mucosal (nasal) immune response generated (nasal IgA antibodies). In patients vaccinated parenterally with an influenza vaccine there are much lower titers of influenza-specific antibodies in the nasal mucosa. Nasal vaccination can provide a mucosal immune response (nasal IgA) that is not generated (or generated only at low levels) by parenteral vaccination. Combining parenteral and nasal vaccination at the same time point may generate a broader immune response compared to vaccinating parenterally alone, or the parenteral administration may be completely substituted with intranasal administration to obtain a sufficient immune response.

The vaccine may include antigen from one A strain, or from two or more A strains, or from at least one B strain, or combinations thereof, or the vaccine may comprise the same antigen in all doses administered.

In some subjects it is difficult to evoke a sufficient immune response and in such cases a boost dose should be given. This is often the case in children (aged 6 months to 8 years) and in the elderly (>50 years), but it is envisaged that many other people would benefit from the boost dose and a stronger and repetitive stimulation of the immune system. However, up to now compositions have not been provided in a form that enables self-administration and, accordingly, only persons of low age or with naïve immune systems (to the specific antigen used in the vaccine, such as in case of pandemics) have been offered a boost dose.

In some cases the intranasally administered prime dose of vaccine gives sufficient immune response and it is not necessary to strengthen the immune response by a parenterally administered dose. In such situations, no medically trained personnel is required to administer the dose as it can easily be self-administered.

In other cases e.g. for persons with not yet fully developed immune systems (children below the age of 5 and even more so below the age of 2) or influenza naïve immune systems (common in children 0-8 years) or persons with immune systems at least partly affected by immunosenescence (older adults and elderly age 50+), the intranasally administered dose of vaccine may not be sufficient to obtain a sufficient immune response. In such cases it may be necessary to stimulate the immune response by a parenterally administered dose (i.e. the prime dose is a combination of intranasal and parenteral administration). As explained above, the focus of the present invention is vaccination, where it is an advantage also to obtain specific nasal immune response (as many viruses or bacteria are air-borne and transmitted via the air-ways to the persons). When such a combined vaccination is required as prime dose, the parenterally administered dose and the intranasally administered dose may be administered by medically educated personnel at the same visit to the medical clinic. This may also be the case in the future, but the provision of a dosage unit form designed for self-administration enables other dosage regimens. Thus, there may be cases where it is advantageous to obtain a nasal immune response as a first response. In such cases the intranasal dose should be administered before the parenterally administered dose. In other situations it may be advantageous to obtain the nasal immune response as a second response. In these cases the intranasal dose should be administered after the parenterally administered dose. However, in both of these situations, the person can administer the intranasal dose by self-administration. In those situations where it is advantageous to administer the two doses at the same point of time, the medically trained personal may administer both doses, but still the advantage having a container with the metered amount of the vaccine composition for intranasal administration makes it much easier to ensure a correct dosing of the vaccine. Moreover, it is needle-free and enables a better compliance.

Many variations with respect to prime and boost dose are known from the literature and are encompassed by the present invention.

If a prime and one or more boost doses are given for influenza vaccination, the time period between the prime and the boost (the first boost dose if more than one boost dose is given) is normally at least 3-5 weeks, but it could also be from 4 weeks to 1 year. However, for practical reasons and to obtain a high enough immune response, fast enough to protect during the flu season, it should be about 3-5 weeks. It is a balance, longer interval between vaccinations might generate a better immune response (at least in children), but then there is a higher chance of being exposed to influenza before having received a boost dose and thus it is more likely that the person gets sick. If further boost doses are given, then the time period between the boost doses normally is at least 3-4 weeks.

The amount of each antigen (e.g. hemagglutinin) in the first prime vaccination composition is in the range of 0.1 to 60 µg per antigen.

The term "comprising" encompasses "including" as well as "consisting". Thus, a composition "comprising" A may consist exclusively of A or may include additional matter e.g. A+B. The term "about" includes the specified amount as well as the specified amount±10%.

The present invention also relates to an administration regimen for intranasal administration of a vaccine composition for use in immunizing a human, the administration regimen comprise:

a) administration of a vaccine composition by use of a first vaccine component, the first vaccine component comprise a first set of one or more containers, where each container comprise the vaccine composition, b) optionally administration of a vaccine composition by use of a second vaccine component, the second vaccine component comprise a second set of one or more containers, where each container comprise the vaccine composition, wherein each container of the first and second set of containers contains a total volume of the vaccine composition from about 5 microliter to about 400 microliter.

The present invention also relates to a device for use in administration of vaccine compositions, the device comprising:

a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter.

The present invention also relates to the use of:

a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter for immunizing a human.

The present invention also relates to the use of:

a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter for the preparation of a vaccine for intranasally immunizing a human.

The present invention also relates to a method of treating a person in need of a vaccination, comprising administering:

a) a first vaccine component comprising i) a first set of one or more containers, each container containing a vaccine composition for intranasal administration, b) optionally a second vaccine component comprising a second set of one or more containers, each container containing a vaccine composition for intranasal administration: wherein each container of the first and second set of containers contains a total volume of the vaccine composition from about 5 microliter to about 400 microliter.

The present invention also relates to a vaccine formulated for intranasal administering comprising:

a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter.

It is to be understood that the above description in relation to the vaccine kit of the invention also apply to:

The administration regimen for intranasal administration of a vaccine composition for use in immunizing a human.

The device for use in administration of vaccine compositions.

The use of: a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter for immunizing a human.

The use of: a) a first vaccine component comprising i) a first set of one or more containers, each container containing a vaccine composition for intranasal administration, b) optionally a second vaccine component comprising a second set of one or more containers, each container containing a vaccine composition for intranasal administration, wherein each container of the first and second set of containers contains a total volume of the vaccine composition from about 5 microliter to about 400 microliter for the preparation of a vaccine for intranasally immunizing a human.

The method of treating a person in need of a vaccination.

The vaccine formulated for intranasal administering.

Experimentals

This experiment relates to a regimen where the prime dose is given both parenterally and intranasally, and the first boost dose is given intranasally. The dose given intranasally may be split in more than one container, e.g. in two containers, where the content of each container is administered to a nostril.

Study Layout:

Mice (Balb/c, female, 7-9 weeks, n=8 per group (n=4 in negative control group)) followed a vaccination schedule where they where vaccinated on day 0, 21 and 42 and sacrifice on day 61. The vaccination dose and volume were as follows: Nasally (i.n.): 1.5 or 0.5 µg HA, 2% Endocine™ in 2×5 µl (5 µl in each nostril). The Endocine™ adjuvant used in the study comprises equimolar amounts of glycerol monooleate and oleic acid with a final concentration of 20 mg/ml in the vaccine composition. Subcutaneous (s.c.): 1.5 or 0.5 µg HA in 50 µl (in the right hind leg). The test substances were split Influenza A/California/07/2009 (H1N1) antigen and Endocine™ adjuvant from Eurocine Vaccines AB. Negative control was saline (sodium chloride) 0.9%. The blood samples and nasal wash samples were collected at day −1, 19, 40 and 61.

The data showed that parenteral immunization is needed to induce IgG2a titers after prime (first dose) as shown in FIGS. 1 and 2. Group B had lower serum IgG2a titers compared to the groups that got a parenteral injection at prime (group A and C). No significant differences could be seen in group A-C after the third dose, however after the first dose group B showed significantly lower serum IgG2a titers compared to the groups that got a parenteral injection at prime (group A and C).

The data in FIGS. 3 and 4 also showed that intranasal immunization is needed to induce IgA titers after second dose.

The conclusion from this study is that parenteral (sc) administration induce higher IgG2a (after prime) and that nasal administration induce higher IgA. The combination of a parenteral and a nasal administration at prime induce a broader immune response.

The specific combination of e.g. parenteral/intranasal administration as a prime dose and intranasal administration of one or more boost doses will depend on the vaccination in question.

The present invention comprise the following different embodiments:

1. A vaccine kit comprising
   a) a first vaccine component comprising i) a first set of one or more containers, each container containing a vaccine composition for intranasal administration,
   b) optionally a second vaccine component comprising a second set of one or more containers, each container containing a vaccine composition for intranasal administration, and
   c) optionally instructions for use,
   wherein each container of the first and second set of containers contains a total volume of the vaccine composition from about 5 microliter to about 400 microliter.

2. A kit according to embodiment 1, wherein the first set of containers has up to 4 containers.

3. A kit according to embodiment 1 or 2, wherein the first vaccine component further contains a vaccine composition for parenteral administration.

4. A kit according to any of the preceding embodiments, wherein the second vaccine component is included in the kit.

5. A kit according to any of the preceding embodiments, wherein the second set of containers has up to 8 containers.

6. A kit according to any of the preceding embodiments, wherein the vaccine composition in the first set of containers is made up of the same ingredients.

7. A kit according to embodiment 6, wherein the concentration and amount of the individual ingredients in the vaccine composition in the first set of containers are the same.

8. A kit according to any of the preceding embodiments, wherein the vaccine composition in the second set of containers is made up of the same ingredients.

9. A kit according to embodiment 8, wherein the concentration and amount of the individual ingredients in the vaccine composition in the second set of containers are the same.

10. A kit according to any of the preceding embodiments, wherein the vaccine composition in the first and second set of containers is made up of the same ingredients.

11. A kit according to embodiment 10, wherein the concentration and amount of the individual ingredients in the vaccine composition in the first and second set of containers are the same.

12. A kit according to any of the preceding embodiments, wherein the vaccine composition for intranasal administration in the first and second component contains one or more antigens.

13. A kit according to any of the preceding embodiments, wherein the vaccine composition for parenteral administration in the first component contains one or more antigens.

14. A kit according to embodiments 12 or 13, wherein the one or more antigens are from inactivated whole bacteria or viruses or parts thereof 15. A kit according to any one of embodiments 12-14, wherein the one or more antigens are from one or more strains of bacteria and/or viruses.

16. A kit according to any one of embodiments 12-15, wherein the vaccine composition contains up to 30 different antigens.

17. A kit according to any one of embodiments 12-16, wherein the vaccine compositions of the first and second component contain the same antigen(s).

18. A kit according to any one of embodiments 12-17, wherein the one or more antigens are antigens inducing an immune response against Influenza A, Influenza B, RSV, Human metapneumovirus (hMPV), HPV, Rotavirus, Norovirus, HIV, Herpes simplex, and/or Parainfluenza virus (OIV), or mixtures thereof 19. A kit according to any one of embodiments 12-18, wherein the one or more antigens are antigens inducing an immune response against Rhino virus, SARS, Coronaviruses, Herpes zoster/varicella, Hepatitis A-E, Hantavirus, and/or Cytomegalovirus, or mixtures thereof 20. A kit according to any one of embodiments 12-19, wherein the one or more antigens are antigens inducing an immune response against Pneumococci and/or Meningococci, or mixtures thereof 21. A kit according to any one of embodiments 12-20, wherein the one or more antigens are antigens inducing an immune response against *Haemophilus influenzae* b, *Bacillus anthracis, Chlamydia trachomatis, Pseudomonas aeruginosa, Mycobacterium tuberculosis,* Diphtheria, *Escherichia coli,* Group *Streptococcus, Neisseria gonorrhoeae* and/or *Bordetella pertussis* or mixtures thereof.

22. A kit according to any one of embodiments 12-21, wherein the one or more antigens are antigens inducing an immune response against diphtheria, tentanus, pertussis, polio, measles, mumps, rubella, cervixal cancer, tuberculosis and/or chickenpox, or mixtures thereof.

23. A kit according to any one of embodiments 12-22, wherein the one or more antigens are antigens inducing an immune response against allergies due to house dust mite, pollen and other environmental allergens, food, insect bite, latex, cosmetic, animals and/or nickel or mixtures thereof.

24. A kit according to any of the preceding embodiments, wherein the volume of the vaccine composition for intranasal administration in each container is from about 50 µl to about 250 µl.

25. A kit according to any of the preceding embodiments, wherein each container containing the vaccine composition for intranasal administration contains 50% or 100% of a vaccination dose.

26. A kit according to any of the preceding embodiments, wherein the first set of containers is two containers, each containing the same vaccine composition and in the same volume.

27. A kit according to any of the preceding embodiments, wherein the second set of containers is two containers, each containing the same vaccine composition and in the same volume.

28. A kit according to any of the preceding embodiments, wherein the vaccine composition for intranasal administration contains an adjuvant.

29. A kit according to any of the preceding embodiments, wherein the vaccine composition for intranasal administration contains one or more of:
 i) a monoester of glycerol with a fatty acid,
 ii) a fatty acid,
 iii) a combination of fatty acids,
 iv) a mixture thereof.

30. A kit according to embodiment 29, wherein the vaccine composition contains a monoester of glycerol with a fatty acid in a concentration of from 5 to 40 mg/ml.

31. A kit according to embodiments 29 or 30, wherein the vaccine composition contains a fatty acid or a combination of fatty acids in a total concentration of from 2 to 40 mg/ml.

32. A kit according to any of the preceding embodiments, wherein the vaccine composition for intranasal administration contains:
 i) a monoester of glycerol with a fatty ester, and
 ii) a fatty acid.

33. A kit according to any of the preceding embodiments, wherein the vaccine composition for intranasal administration contains:
 i) glycerol monooleate, and
 ii) oleic acid.

34. A kit according to embodiment 33, wherein the concentration of glycerol monooleate is from 2.5 to 20 mg/ml and the concentration of oleic acid is from 2.5 to 20 mg/ml in the vaccine composition.

35. A kit according to any of the preceding embodiments, wherein the vaccine composition for intranasal administration is given by self-administration.

36. A set of containers as defined in any of the preceding embodiments for vaccination by self-administration to the nose.

37. An administration regimen for intranasal administration of a vaccine composition for use in immunizing a human, the administration regimen comprise:
 a) administration of a vaccine composition by use of a first vaccine component, the first vaccine component comprise a first set of one or more containers, where each container comprise the vaccine composition,
 b) optionally administration of a vaccine composition by use of a second vaccine component, the second vaccine component comprise a second set of one or more containers, where each container comprise the vaccine composition,
 wherein each container of the first and second set of containers contains a total volume of the vaccine composition from about 5 microliter to about 400 microliter.

38. An administration regimen for intranasal administration of a vaccine composition for use in immunizing a human according to embodiment 37, wherein the first set of containers has up to 4 containers.

39. An administration regimen for intranasal administration of a vaccine composition for use in immunizing a human according to embodiment 37 or 38, wherein the first vaccine component further contains a vaccine composition for parenteral administration.

40. An administration regimen for intranasal administration of a vaccine composition for use in immunizing a human according to any of the preceding embodiments, wherein the second vaccine component is included in the administration regimen for intranasal administration of a vaccine composition for use in immunizing a human.

41. An administration regimen for intranasal administration of a vaccine composition for use in immunizing a human according to any of the preceding embodiments, wherein the second set of containers has up to 8 containers.

42. An administration regimen for intranasal administration of a vaccine composition for use in immunizing a human according to any of the preceding embodiments, wherein the vaccine composition in the first set of containers is made up of the same ingredients.

43. An administration regimen for intranasal administration of a vaccine composition for use in immunizing a human according to embodiment 42, wherein the concentration and amount of the individual ingredients in the vaccine composition in the first set of containers are the same.

44. An administration regimen for intranasal administration of a vaccine composition for use in immunizing a human according to any of the preceding embodiments, wherein the vaccine composition in the second set of containers is made up of the same ingredients.

45. An administration regimen for intranasal administration of a vaccine composition for use in immunizing a human according to embodiment 44, wherein the concentration and amount of the individual ingredients in the vaccine composition in the second set of containers are the same.

46. An administration regimen for intranasal administration of a vaccine composition for use in immunizing a human according to any of the preceding embodiments, wherein the vaccine composition in the first and second set of containers is made up of the same ingredients.

47. An administration regimen for intranasal administration of a vaccine composition for use in immunizing a human according to embodiment 46, wherein the concentration and amount of the individual ingredients in the vaccine composition in the first and second set of containers are the same.

48. An administration regimen for intranasal administration of a vaccine composition for use in immunizing a human according to any of the preceding embodiments, wherein the vaccine composition for intranasal administration in the first and second component contains one or more antigens.

49. An administration regimen for intranasal administration of a vaccine composition for use in immunizing a human according to any of the preceding embodiments, wherein the vaccine composition for parenteral administration in the first component contains one or more antigens.

50. An administration regimen for intranasal administration of a vaccine composition for use in immunizing a human according to embodiments 48 or 49, wherein the one or more antigens are from inactivated whole bacteria or viruses or parts thereof 51. An administration regimen for intranasal administration of a vaccine composition for use in immunizing a human according to any one of embodiments 48-50, wherein the one or more antigens are from one or more strains of bacteria and/or viruses.

52. An administration regimen for intranasal administration of a vaccine composition for use in immunizing a human according to any one of embodiments 48-51, wherein the vaccine composition contains up to 30 different antigens.

53. An administration regimen for intranasal administration of a vaccine composition for use in immunizing a human according to any one of embodiments 48-52, wherein the vaccine compositions of the first and second component contain the same antigen(s).

54. An administration regimen for intranasal administration of a vaccine composition for use in immunizing a human according to any one of embodiments 48-53, wherein the one or more antigens are antigens inducing an immune response against Influenza A, Influenza B, RSV, Human metapneumovirus (hMPV), HPV, Rotavirus, Norovirus, HIV, Herpes simplex, and/or Parainfluenza virus (OIV), or mixtures thereof.

55. An administration regimen for intranasal administration of a vaccine composition for use in immunizing a human according to any one of embodiments 48-53, wherein the one or more antigens are antigens inducing an immune response against Rhino virus, SARS, Coronaviruses, Herpes zoster/varicella, Hepatitis A-E, Hantavirus, and/or Cytomegalovirus, or mixtures thereof.

56. An administration regimen for intranasal administration of a vaccine composition for use in immunizing a human according to any one of embodiments 48-55, wherein the one or more antigens are antigens inducing an immune response against Pneumococci and/or Meningococci, or mixtures thereof.

57. An administration regimen for intranasal administration of a vaccine composition for use in immunizing a human according to any one of embodiments 48-56, wherein the one or more antigens are antigens inducing an immune response against *Haemophilus influenzae* b, *Bacillus anthracis*, *Chlamydia trachomatis*, *Pseudomonas aeruginosa*, *Mycobacterium tuberculosis*, Diphtheria, *Escherichia coli*, Group *Streptococcus*, *Neisseria gonorrhoeae* and/or *Bordetella pertussis* or mixtures thereof 58. An administration regimen for intranasal administration of a vaccine composition for use in immunizing a human according to any one of embodiments 48-57, wherein the one or more antigens are antigens inducing an immune response against diphtheria, tentanus, pertussis, polio, measles, mumps, rubella, cervixal cancer, tuberculosis and/or chickenpox, or mixtures thereof.

59. An administration regimen for intranasal administration of a vaccine composition for use in immunizing a human according to any one of embodiments 48-58, wherein the one or more antigens are antigens inducing an immune response against allergies due to house dust mite, pollen and other environmental allergens, food, insect bite, latex, cosmetic, animals and/or nickel or mixtures thereof.

60. An administration regimen for intranasal administration of a vaccine composition for use in immunizing a human according to any of the preceding embodiments, wherein the volume of the vaccine composition for intranasal administration in each container is from about 50 µl to about 250 µl.

61. An administration regimen for intranasal administration of a vaccine composition for use in immunizing a human according to any of the preceding embodiments, wherein each container containing the vaccine composition for intranasal administration contains 50% or 100% of a vaccination dose.

62. An administration regimen for intranasal administration of a vaccine composition for use in immunizing a human according to any of the preceding embodiments, wherein the first set of containers is two containers, each containing the same vaccine composition and in the same volume.

63. An administration regimen for intranasal administration of a vaccine composition for use in immunizing a human according to any of the preceding embodiments, wherein the second set of containers is two containers, each containing the same vaccine composition and in the same volume.

64. An administration regimen for intranasal administration of a vaccine composition for use in immunizing a human according to any of the preceding embodiments, wherein the vaccine composition for intranasal administration contains an adjuvant.

65. An administration regimen for intranasal administration of a vaccine composition for use in immunizing a human according to any of the preceding embodiments, wherein the vaccine composition for intranasal administration contains one or more of:
  i) a monoester of glycerol with a fatty acid,
  ii) a fatty acid,
  iii) a combination of fatty acids,
  iv) a mixture thereof 66. An administration regimen for intranasal administration of a vaccine composition for use in immunizing a human according to embodiment 65, wherein the vaccine composition contains a monoester of glycerol with a fatty acid in a concentration of from 5 to 40 mg/ml.

67. An administration regimen for intranasal administration of a vaccine composition for use in immunizing a human according to embodiments 65 or 66, wherein the vaccine composition contains a fatty acid or a combination of fatty acids in a total concentration of from 2 to 40 mg/ml.

68. An administration regimen for intranasal administration of a vaccine composition for use in immunizing a human according to any of the preceding embodiments, wherein the vaccine composition for intranasal administration contains:
  i) a monoester of glycerol with a fatty ester, and
  ii) a fatty acid.

69. An administration regimen for intranasal administration of a vaccine composition for use in immunizing a human according to any of the preceding embodiments, wherein the vaccine composition for intranasal administration contains:
  i) glycerol monooleate, and
  ii) oleic acid.

70. An administration regimen for intranasal administration of a vaccine composition for use in immunizing a human according to embodiment 69, wherein the concentration of glycerol monooleate is from 2.5 to 20 mg/ml and the concentration of oleic acid is from 2.5 to 20 mg/ml in the vaccine composition.

71. An administration regimen for intranasal administration of a vaccine composition for use in immunizing a human according to any of the preceding embodiments, wherein the vaccine composition for intranasal administration is given by self-administration.

72. A device for use in administration of vaccine compositions, the device comprising:
  a) a first vaccine component comprising i) a first set of one or more containers, each container containing a vaccine composition for intranasal administration,
  b) optionally a second vaccine component comprising a second set of one or more containers, each container containing a vaccine composition for intranasal administration, wherein each container of the first and second set of containers contains a total volume of the vaccine composition from about 5 microliter to about 400 microliter.

73. A device according to embodiment 72, wherein the first set of containers has up to 4 containers.

74. A device according to embodiment 72 or 73, wherein the first vaccine component further contains a vaccine composition for parenteral administration.

75. A device according to any of the preceding embodiments, wherein the second vaccine component is included in the device.

76. A device according to any of the preceding embodiments, wherein the second set of containers has up to 8 containers.

77. A device according to any of the preceding embodiments, wherein the vaccine composition in the first set of containers is made up of the same ingredients.

78. A device according to embodiment 77, wherein the concentration and amount of the individual ingredients in the vaccine composition in the first set of containers are the same.

79. A device according to any of the preceding embodiments, wherein the vaccine composition in the second set of containers is made up of the same ingredients.

80. A device according to embodiment 79, wherein the concentration and amount of the individual ingredients in the vaccine composition in the second set of containers are the same.

81. A device according to any of the preceding embodiments, wherein the vaccine composition in the first and second set of containers is made up of the same ingredients.

82. A device according to embodiment 81, wherein the concentration and amount of the individual ingredients in the vaccine composition in the first and second set of containers are the same.

83. A device according to any of the preceding embodiments, wherein the vaccine composition for intranasal administration in the first and second component contains one or more antigens.

84. A device according to any of the preceding embodiments, wherein the vaccine composition for parenteral administration in the first component contains one or more antigens.

85. A device according to embodiments 83 or 84, wherein the one or more antigens are from inactivated whole bacteria or viruses or parts thereof.

86. A device according to any one of embodiments 83-85, wherein the one or more antigens are from one or more strains of bacteria and/or viruses.

87. A device according to any one of embodiments 83-86, wherein the vaccine composition contains up to 30 different antigens.

88. A device according to any one of embodiments 83-87, wherein the vaccine compositions of the first and second component contain the same antigen(s).

89. A device according to any one of embodiments 83-88, wherein the one or more antigens are antigens inducing an immune response against Influenza A, Influenza B, RSV, Human metapneumovirus (hMPV), HPV, Rotavirus, Norovirus, HIV, Herpes simplex, and/or Parainfluenza virus (OIV), or mixtures thereof.

90. A device according to any one of embodiments 83-89, wherein the one or more antigens are antigens inducing an immune response against Rhino virus, SARS, Coronaviruses, Herpes zoster/varicella, Hepatitis A-E, Hantavirus, and/or Cytomegalovirus, or mixtures thereof.

91. A device according to any one of embodiments 83-90, wherein the one or more antigens are antigens inducing an immune response against Pneumococci and/or Meningococci, or mixtures thereof.

92. A device according to any one of embodiments 83-91, wherein the one or more antigens are antigens inducing an immune response against *Haemophilus influenzae* b, *Bacillus anthracis, Chlamydia trachomatis, Pseudomonas aeruginosa, Mycobacterium tuberculosis,* Diphtheria, *Escherichia coli,* Group *Streptococcus, Neisseria gonorrhoeae* and/or *Bordetella pertussis* or mixtures thereof.

93. A device according to any one of embodiments 83-92, wherein the one or more antigens are antigens inducing an immune response against diphtheria, tentanus, pertussis, polio, measles, mumps, rubella, cervixal cancer, tuberculosis and/or chickenpox, or mixtures thereof.

94. A device according to any one of embodiments 83-93, wherein the one or more antigens are antigens inducing an immune response against allergies due to house dust mite, pollen and other environmental allergens, food, insect bite, latex, cosmetic, animals and/or nickel or mixtures thereof 95. A device according to any of the preceding embodiments, wherein the volume of the vaccine composition for intranasal administration in each container is from about 50 µl to about 250 µl.

96. A device according to any of the preceding embodiments, wherein each container containing the vaccine composition for intranasal administration contains 50% or 100% of a vaccination dose.

97. A device according to any of the preceding embodiments, wherein the first set of containers is two containers, each containing the same vaccine composition and in the same volume.

98. A device according to any of the preceding embodiments, wherein the second set of containers is two containers, each containing the same vaccine composition and in the same volume.

99. A device according to any of the preceding embodiments, wherein the vaccine composition for intranasal administration contains an adjuvant.

100. A device according to any of the preceding embodiments, wherein the vaccine composition for intranasal administration contains one or more of:
   i) a monoester of glycerol with a fatty acid,
   ii) a fatty acid,
   iii) a combination of fatty acids,
   iv) a mixture thereof.

101. A device according to embodiment 100, wherein the vaccine composition contains a monoester of glycerol with a fatty acid in a concentration of from 5 to 40 mg/ml.

102. A device according to embodiments 100 or 101, wherein the vaccine composition contains a fatty acid or a combination of fatty acids in a total concentration of from 2 to 40 mg/ml.

103. A device according to any of the preceding embodiments, wherein the vaccine composition for intranasal administration contains:
   i) a monoester of glycerol with a fatty ester, and
   ii) a fatty acid.

104. A device according to any of the preceding embodiments, wherein the vaccine composition for intranasal administration contains:
   i) glycerol monooleate, and
   ii) oleic acid.

105. A device according to embodiment 104, wherein the concentration of glycerol monooleate is from 2.5 to 20 mg/ml and the concentration of oleic acid is from 2.5 to 20 mg/ml in the vaccine composition.

106. A device according to any of the preceding embodiments, wherein the vaccine composition for intranasal administration is given by self-administration.

107. Use of:
   a) a first vaccine component comprising i) a first set of one or more containers, each container containing a vaccine composition for intranasal administration,
   b) optionally a second vaccine component comprising a second set of one or more containers, each container containing a vaccine composition for intranasal administration, wherein each container of the first and second set of containers contains a total volume of the vaccine composition from about 5 microliter to about 400 microliter for immunizing a human.

108. The use according to embodiment 107, wherein the first set of containers has up to 4 containers.

109. The use according to embodiment 107 or 108, wherein the first vaccine component further contains a vaccine composition for parenteral administration.

110. The use according to any of the preceding embodiments, wherein the second vaccine component is included in the use.

111. The use according to any of the preceding embodiments, wherein the second set of containers has up to 8 containers.

112. The use according to any of the preceding embodiments, wherein the vaccine composition in the first set of containers is made up of the same ingredients.

113. The use according to embodiment 112, wherein the concentration and amount of the individual ingredients in the vaccine composition in the first set of containers are the same.

114. The use according to any of the preceding embodiments, wherein the vaccine composition in the second set of containers is made up of the same ingredients.

115. A kit according to embodiment 114, wherein the concentration and amount of the individual ingredients in the vaccine composition in the second set of containers are the same.

116. The use according to any of the preceding embodiments, wherein the vaccine composition in the first and second set of containers is made up of the same ingredients.

117. The use according to embodiment 116, wherein the concentration and amount of the individual ingredients in the vaccine composition in the first and second set of containers are the same.

118. The use according to any of the preceding embodiments, wherein the vaccine composition for intranasal administration in the first and second component contains one or more antigens.

119. The use according to any of the preceding embodiments, wherein the vaccine composition for parenteral administration in the first component contains one or more antigens.

120. The use according to embodiments 118 or 119, wherein the one or more antigens are from inactivated whole bacteria or viruses or parts thereof.

121. The use according to any one of embodiments 118-120, wherein the one or more antigens are from one or more strains of bacteria and/or viruses.

122. The use according to any one of embodiments 118-121, wherein the vaccine composition contains up to 30 different antigens.

123. The use according to any one of embodiments 118-122, wherein the vaccine compositions of the first and second component contain the same antigen(s).

124. The use according to any one of embodiments 118-123, wherein the one or more antigens are antigens inducing an immune response against Influenza A, Influenza B, RSV, Human metapneumovirus (hMPV), HPV, Rotavirus, Norovirus, HIV, Herpes simplex, and/or Parainfluenza virus (OIV), or mixtures thereof.

125. The use according to any one of embodiments 118-124, wherein the one or more antigens are antigens inducing an immune response against Rhino virus, SARS, Coronaviruses, Herpes zoster/varicella, Hepatitis A-E, Hantavirus, and/or Cytomegalovirus, or mixtures thereof.

126. The use it according to any one of embodiments 118-125, wherein the one or more antigens are antigens inducing an immune response against Pneumococci and/or Meningococci, or mixtures thereof.

127. The use according to any one of embodiments 118-126, wherein the one or more antigens are antigens inducing an immune response against *Haemophilus influenzae* b, *Bacillus anthracis, Chlamydia trachomatis, Pseudomonas aeruginosa, Mycobacterium tuberculosis*, Diphtheria, *Escherichia coli*, Group *Streptococcus, Neisseria gonorrhoeae* and/or *Bordetella pertussis* or mixtures thereof.

128. The use according to any one of embodiments 118-127, wherein the one or more antigens are antigens inducing an immune response against diphtheria, tentanus, pertussis, polio, measles, mumps, rubella, cervixal cancer, tuberculosis and/or chickenpox, or mixtures thereof.

129. The use according to any one of embodiments 118-128, wherein the one or more antigens are antigens inducing an immune response against allergies due to house dust mite, pollen and other environmental allergens, food, insect bite, latex, cosmetic, animals and/or nickel or mixtures thereof.

130. The use according to any of the preceding embodiments, wherein the volume of the vaccine composition for intranasal administration in each container is from about 50 µl to about 250 µl.

131. The use according to any of the preceding embodiments, wherein each container containing the vaccine composition for intranasal administration contains 50% or 100% of a vaccination dose.

132. The use according to any of the preceding embodiments, wherein the first set of containers is two containers, each containing the same vaccine composition and in the same volume.

133. The use according to any of the preceding embodiments, wherein the second set of containers is two containers, each containing the same vaccine composition and in the same volume.

134. The use according to any of the preceding embodiments, wherein the vaccine composition for intranasal administration contains an adjuvant.

135. The use according to any of the preceding embodiments, wherein the vaccine composition for intranasal administration contains one or more of:
  i) a monoester of glycerol with a fatty acid,
  ii) a fatty acid,
  iii) a combination of fatty acids,
  iv) a mixture thereof.

136. The use according to embodiment 135, wherein the vaccine composition contains a monoester of glycerol with a fatty acid in a concentration of from 5 to 40 mg/ml.

137. The use according to embodiments 135 or 136, wherein the vaccine composition contains a fatty acid or a combination of fatty acids in a total concentration of from 2 to 40 mg/ml.

138. The use according to any of the preceding embodiments, wherein the vaccine composition for intranasal administration contains:
  i) a monoester of glycerol with a fatty ester, and
  ii) a fatty acid.

139. The use according to any of the preceding embodiments, wherein the vaccine composition for intranasal administration contains:
  i) glycerol monooleate, and
  ii) oleic acid.

140. The use according to embodiment 139, wherein the concentration of glycerol monooleate is from 2.5 to 20 mg/ml and the concentration of oleic acid is from 2.5 to 20 mg/ml in the vaccine composition.

141. The use according to any of the preceding embodiments, wherein the vaccine composition for intranasal administration is given by self-administration.

142. Use of:
  a) a first vaccine component comprising i) a first set of one or more containers, each container containing a vaccine composition for intranasal administration,
  b) optionally a second vaccine component comprising a second set of one or more containers, each container containing a vaccine composition for intranasal administration, wherein each container of the first and second set of containers contains a total volume of the vaccine composition from about 5 microliter to about 400 microliter for the preparation of a vaccine for intranasally immunizing a human.

143. The use according to embodiment 142, wherein the first set of containers has up to 4 containers.

144. The use according to embodiment 132 or 133, wherein the first vaccine component further contains a vaccine composition for parenteral administration.

145. The use according to any of the preceding embodiments, wherein the second vaccine component is included in the use.

146. The use according to any of the preceding embodiments, wherein the second set of containers has up to 8 containers.

147. The use according to any of the preceding embodiments, wherein the vaccine composition in the first set of containers is made up of the same ingredients.

148. The use according to embodiment 147, wherein the concentration and amount of the individual ingredients in the vaccine composition in the first set of containers are the same.

149. The use according to any of the preceding embodiments, wherein the vaccine composition in the second set of containers is made up of the same ingredients.

150. The use according to embodiment 149, wherein the concentration and amount of the individual ingredients in the vaccine composition in the second set of containers are the same.

151. The use according to any of the preceding embodiments, wherein the vaccine composition in the first and second set of containers is made up of the same ingredients.

152. The use according to embodiment 151, wherein the concentration and amount of the individual ingredients in the vaccine composition in the first and second set of containers are the same.

153. The use according to any of the preceding embodiments, wherein the vaccine composition for intranasal administration in the first and second component contains one or more antigens.

154. The use according to any of the preceding embodiments, wherein the vaccine composition for parenteral administration in the first component contains one or more antigens.

155. The use according to embodiments 153 or 154, wherein the one or more antigens are from inactivated whole bacteria or viruses or parts thereof.

156. The use according to any one of embodiments 153-155, wherein the one or more antigens are from one or more strains of bacteria and/or viruses.

157. The use according to any one of embodiments 153-156, wherein the vaccine composition contains up to 30 different antigens.

158. The use according to any one of embodiments 153-157, wherein the vaccine compositions of the first and second component contain the same antigen(s).

159. The use according to any one of embodiments 153-158, wherein the one or more antigens are antigens inducing an immune response against Influenza A, Influenza B, RSV, Human metapneumovirus (hMPV), HPV, Rotavirus, Norovirus, HIV, Herpes simplex, and/or Parainfluenza virus (OIV), or mixtures thereof.

160. The use according to any one of embodiments 153-159, wherein the one or more antigens are antigens inducing an immune response against Rhino virus, SARS, Coronaviruses, Herpes zoster/varicella, Hepatitis A-E, Hantavirus, and/or Cytomegalovirus, or mixtures thereof.

161. The use according to any one of embodiments 153-160, wherein the one or more antigens are antigens inducing an immune response against Pneumococci and/or Meningococci, or mixtures thereof.

162. The use according to any one of embodiments 153-161, wherein the one or more antigens are antigens inducing an immune response against *Haemophilus influenzae* b, *Bacillus anthracis*, *Chlamydia trachomatis*, *Pseudomonas aeruginosa*, *Mycobacterium tuberculosis*, Diphtheria, *Escherichia coli*, Group *Streptococcus*, *Neisseria gonorrhoeae* and/or *Bordetella pertussis* or mixtures thereof.

163. The use according to any one of embodiments 153-162, wherein the one or more antigens are antigens inducing an immune response against diphtheria, tentanus, pertussis, polio, measles, mumps, rubella, cervixal cancer, tuberculosis and/or chickenpox, or mixtures thereof.

164. The use according to any one of embodiments 153-163 wherein the one or more antigens are antigens inducing an immune response against allergies due to house dust mite, pollen and other environmental allergens, food, insect bite, latex, cosmetic, animals and/or nickel or mixtures thereof.

165. The use according to any of the preceding embodiments, wherein the volume of the vaccine composition for intranasal administration in each container is from about 50 μl to about 250 μl.

166. The use according to any of the preceding embodiments, wherein each container containing the vaccine composition for intranasal administration contains 50% or 100% of a vaccination dose.

167. The use according to any of the preceding embodiments, wherein the first set of containers is two containers, each containing the same vaccine composition and in the same volume.

168. The use according to any of the preceding embodiments, wherein the second set of containers is two containers, each containing the same vaccine composition and in the same volume.

169. The use according to any of the preceding embodiments, wherein the vaccine composition for intranasal administration contains an adjuvant.

170. The use according to any of the preceding embodiments, wherein the vaccine composition for intranasal administration contains one or more of:
  i) a monoester of glycerol with a fatty acid,
  ii) a fatty acid,
  iii) a combination of fatty acids,
  iv) a mixture thereof.

171. The use according to embodiment 170, wherein the vaccine composition contains a monoester of glycerol with a fatty acid in a concentration of from 5 to 40 mg/ml.

172. The use according to embodiments 170 or 171, wherein the vaccine composition contains a fatty acid or a combination of fatty acids in a total concentration of from 2 to 40 mg/ml.

173. The use according to any of the preceding embodiments, wherein the vaccine composition for intranasal administration contains:
  i) a monoester of glycerol with a fatty ester, and
  ii) a fatty acid.

174. The use according to any of the preceding embodiments, wherein the vaccine composition for intranasal administration contains:
  i) glycerol monooleate, and
  ii) oleic acid.

175. The use according to embodiment 174, wherein the concentration of glycerol monooleate is from 2.5 to 20 mg/ml and the concentration of oleic acid is from 2.5 to 20 mg/ml in the vaccine composition.

176. The use according to any of the preceding embodiments, wherein the vaccine composition for intranasal administration is given by self-administration.

177. A method of treating a person in need of a vaccination, comprising administering
  a) a first vaccine component comprising i) a first set of one or more containers, each container containing a vaccine composition for intranasal administration,
  b) optionally a second vaccine component comprising a second set of one or more containers, each container containing a vaccine composition for intranasal administration:
  wherein each container of the first and second set of containers contains a total volume of the vaccine composition from about 5 microliter to about 400 microliter.

178. A method according to embodiment 177, wherein the first set of containers has up to 4 containers.

179. A method according to embodiment 177 or 178, wherein the first vaccine component further contains a vaccine composition for parenteral administration.

180. A method according to any of the preceding embodiments, wherein the second vaccine component is included in the method.

181. A method according to any of the preceding embodiments, wherein the second set of containers has up to 8 containers.

182. A method according to any of the preceding embodiments, wherein the vaccine composition in the first set of containers is made up of the same ingredients.

183. A method according to embodiment 182, wherein the concentration and amount of the individual ingredients in the vaccine composition in the first set of containers are the same.

184. A method according to any of the preceding embodiments, wherein the vaccine composition in the second set of containers is made up of the same ingredients.

185. A method according to embodiment 184, wherein the concentration and amount of the individual ingredients in the vaccine composition in the second set of containers are the same.

186. A method according to any of the preceding embodiments, wherein the vaccine composition in the first and second set of containers is made up of the same ingredients.

187. A method according to embodiment 186, wherein the concentration and amount of the individual ingredients in the vaccine composition in the first and second set of containers are the same.

188. A method according to any of the preceding embodiments, wherein the vaccine composition for intranasal administration in the first and second component contains one or more antigens.

189. A method according to any of the preceding embodiments, wherein the vaccine composition for parenteral administration in the first component contains one or more antigens.

190. A method according to embodiments 188 or 189, wherein the one or more antigens are from inactivated whole bacteria or viruses or parts thereof.

191. A method according to any one of embodiments 188-190, wherein the one or more antigens are from one or more strains of bacteria and/or viruses.

192. A method according to any one of embodiments 188-191, wherein the vaccine composition contains up to 30 different antigens.

193. A method according to any one of embodiments 188-192, wherein the vaccine compositions of the first and second component contain the same antigen(s).

194. A method according to any one of embodiments 188-193, wherein the one or more antigens are antigens inducing an immune response against Influenza A, Influenza B, RSV, Human metapneumovirus (hMPV), HPV, Rotavirus, Norovirus, HIV, Herpes simplex, and/or Parainfluenza virus (OIV), or mixtures thereof.

195. A method according to any one of embodiments 188-194, wherein the one or more antigens are antigens inducing an immune response against Rhino virus, SARS, Coronaviruses, Herpes zoster/varicella, Hepatitis A-E, Hantavirus, and/or Cytomegalovirus, or mixtures thereof.

196. A method according to any one of embodiments 188-195, wherein the one or more antigens are antigens inducing an immune response against Pneumococci and/or Meningococci, or mixtures thereof.

197. A method according to any one of embodiments 188-196, wherein the one or more antigens are antigens inducing an immune response against *Haemophilus influenzae* b, *Bacillus anthracis*, *Chlamydia trachomatis*, *Pseudomonas aeruginosa*, *Mycobacterium tuberculosis*, Diphtheria, *Escherichia coli*, Group *Streptococcus*, *Neisseria gonorrhoeae* and/or *Bordetella pertussis* or mixtures thereof.

198. A method according to any one of embodiments 188-197, wherein the one or more antigens are antigens inducing an immune response against diphtheria, tentanus, pertussis, polio, measles, mumps, rubella, cervixal cancer, tuberculosis and/or chickenpox, or mixtures thereof.

199. A method according to any one of embodiments 188-198, wherein the one or more antigens are antigens inducing an immune response against allergies due to house dust mite, pollen and other environmental allergens, food, insect bite, latex, cosmetic, animals and/or nickel or mixtures thereof.

200. A method according to any of the preceding embodiments, wherein the volume of the vaccine composition for intranasal administration in each container is from about 50 µl to about 250 µl.

201. A method according to any of the preceding embodiments, wherein each container containing the vaccine composition for intranasal administration contains 50% or 100% of a vaccination dose.

202. A method according to any of the preceding embodiments, wherein the first set of containers is two containers, each containing the same vaccine composition and in the same volume.

203. A method according to any of the preceding embodiments, wherein the second set of containers is two containers, each containing the same vaccine composition and in the same volume.

204. A method according to any of the preceding embodiments, wherein the vaccine composition for intranasal administration contains an adjuvant.

205. A method according to any of the preceding embodiments, wherein the vaccine composition for intranasal administration contains one or more of:
  i) a monoester of glycerol with a fatty acid,
  ii) a fatty acid,
  iii) a combination of fatty acids,
  iv) a mixture thereof.

206. A method according to embodiment 205, wherein the vaccine composition contains a monoester of glycerol with a fatty acid in a concentration of from 5 to 40 mg/ml.

207. A method according to embodiments 205 or 206, wherein the vaccine composition contains a fatty acid or a combination of fatty acids in a total concentration of from 2 to 40 mg/ml.

208. A method according to any of the preceding embodiments, wherein the vaccine composition for intranasal administration contains:
  i) a monoester of glycerol with a fatty ester, and
  ii) a fatty acid.

209. A method according to any of the preceding embodiments, wherein the vaccine composition for intranasal administration contains:
  i) glycerol monooleate, and
  ii) oleic acid.

210. A method according to embodiment 209, wherein the concentration of glycerol monooleate is from 2.5 to 20 mg/ml and the concentration of oleic acid is from 2.5 to 20 mg/ml in the vaccine composition.

211. A method according to any of the preceding embodiments, wherein the vaccine composition for intranasal administration is given by self-administration.

212. A vaccine formulated for intranasal adminstering comprising
  a) a first vaccine component comprising i) a first set of one or more containers, each container containing a vaccine composition for intranasal administration,
  b) optionally a second vaccine component comprising a second set of one or more containers, each container containing a vaccine composition for intranasal administration, wherein each container of the first and second set of containers contains a total volume of the vaccine composition from about 5 microliter to about 400 microliter.

213. A vaccine according to embodiment 212, wherein the first set of containers has up to 4 containers.

214. A vaccine according to embodiment 212 or 213, wherein the first vaccine component further contains a vaccine composition for parenteral administration.

215. A vaccine according to any of the preceding embodiments, wherein the second vaccine component is included in the vaccine.

216. A vaccine according to any of the preceding embodiments, wherein the second set of containers has up to 8 containers.

217. A vaccine according to any of the preceding embodiments, wherein the vaccine composition in the first set of containers is made up of the same ingredients.

218. A vaccine according to embodiment 217, wherein the concentration and amount of the individual ingredients in the vaccine composition in the first set of containers are the same.

219. A vaccine according to any of the preceding embodiments, wherein the vaccine composition in the second set of containers is made up of the same ingredients.

220. A vaccine according to embodiment 219, wherein the concentration and amount of the individual ingredients in the vaccine composition in the second set of containers are the same.

221. A vaccine according to any of the preceding embodiments, wherein the vaccine composition in the first and second set of containers is made up of the same ingredients.

222. A vaccine according to embodiment 221, wherein the concentration and amount of the individual ingredients in the vaccine composition in the first and second set of containers are the same.

223. A vaccine according to any of the preceding embodiments, wherein the vaccine composition for intranasal administration in the first and second component contains one or more antigens.

224. A vaccine according to any of the preceding embodiments, wherein the vaccine composition for parenteral administration in the first component contains one or more antigens.

225. A vaccine according to embodiments 223 or 224, wherein the one or more antigens are from inactivated whole bacteria or viruses or parts thereof.

226. A vaccine according to any one of embodiments 223-225, wherein the one or more antigens are from one or more strains of bacteria and/or viruses.

227. A vaccine according to any one of embodiments 223-226, wherein the vaccine composition contains up to 30 different antigens.

228. A vaccine according to any one of embodiments 223-227, wherein the vaccine compositions of the first and second component contain the same antigen(s).

229. A vaccine according to any one of embodiments 223-228, wherein the one or more antigens are antigens inducing an immune response against Influenza A, Influenza B, RSV, Human metapneumovirus (hMPV), HPV, Rotavirus, Norovirus, HIV, Herpes simplex, and/or Parainfluenza virus (OIV), or mixtures thereof.

230. A vaccine according to any one of embodiments 223-229, wherein the one or more antigens are antigens inducing an immune response against Rhino virus, SARS, Coronaviruses, Herpes zoster/varicella, Hepatitis A-E, Hantavirus, and/or Cytomegalovirus, or mixtures thereof.

231. A vaccine according to any one of embodiments 223-230, wherein the one or more antigens are antigens inducing an immune response against Pneumococci and/or Meningococci, or mixtures thereof.

232. A vaccine according to any one of embodiments 223-231, wherein the one or more antigens are antigens inducing an immune response against *Haemophilus influenzae* b, *Bacillus anthracis, Chlamydia trachomatis, Pseudomonas aeruginosa, Mycobacterium tuberculosis*, Diphtheria, *Escherichia coli*, Group *Streptococcus, Neisseria gonorrhoeae* and/or *Bordetella pertussis* or mixtures thereof.

233. A vaccine according to any one of embodiments 223-232, wherein the one or more antigens are antigens inducing an immune response against diphtheria, tentanus, pertussis, polio, measles, mumps, rubella, cervixal cancer, tuberculosis and/or chickenpox, or mixtures thereof 234. A vaccine according to any one of embodiments 223-233, wherein the one or more antigens are antigens inducing an immune response against allergies due to house dust mite, pollen and other environmental allergens, food, insect bite, latex, cosmetic, animals and/or nickel or mixtures thereof.

235. A vaccine according to any of the preceding embodiments, wherein the volume of the vaccine composition for intranasal administration in each container is from about 50 μl to about 250 μl.

236. A vaccine according to any of the preceding embodiments, wherein each container containing the vaccine composition for intranasal administration contains 50% or 100% of a vaccination dose.

237. A vaccine according to any of the preceding embodiments, wherein the first set of containers is two containers, each containing the same vaccine composition and in the same volume.

238. A vaccine according to any of the preceding embodiments, wherein the second set of containers is two containers, each containing the same vaccine composition and in the same volume.

239. A vaccine according to any of the preceding embodiments, wherein the vaccine composition for intranasal administration contains an adjuvant.

240. A vaccine according to any of the preceding embodiments, wherein the vaccine composition for intranasal administration contains one or more of:
   i) a monoester of glycerol with a fatty acid,
   ii) a fatty acid,
   iii) a combination of fatty acids,
   iv) a mixture thereof.

241. A vaccine according to embodiment 240, wherein the vaccine composition contains a monoester of glycerol with a fatty acid in a concentration of from 5 to 40 mg/ml.

242. A vaccine according to embodiments 240 or 241, wherein the vaccine composition contains a fatty acid or a combination of fatty acids in a total concentration of from 2 to 40 mg/ml.

243. A vaccine according to any of the preceding embodiments, wherein the vaccine composition for intranasal administration contains:
   i) a monoester of glycerol with a fatty ester, and
   ii) a fatty acid.

244. A vaccine according to any of the preceding embodiments, wherein the vaccine composition for intranasal administration contains:
   i) glycerol monooleate, and
   ii) oleic acid.

245. A vaccine according to embodiment 244, wherein the concentration of glycerol monooleate is from 2.5 to 20 mg/ml and the concentration of oleic acid is from 2.5 to 20 mg/ml in the vaccine composition.

246. A vaccine according to any of the preceding embodiments, wherein the vaccine composition for intranasal administration is given by self-administration.

The invention claimed is:

1. An immunogenic composition comprising:
   a) a prime dose comprising a first immunogenic composition formulated for parenteral administration and further a second immunogenic composition formulated for intranasal administration in a first set of one or more containers, wherein the first immunogenic composition formulated for parenteral administration and the second immunogenic composition formulated for intranasal administration contain one or more antigens from inactivated whole influenza A, influenza B or parts thereof, and
   b) a boost dose comprising a third immunogenic composition formulated for intranasal administration in a second set of one or more containers, wherein said third immunogenic composition formulated for intranasal administration contains one or more antigens from inactivated whole influenza A, influenza B or parts thereof, and
   wherein each of the second and third immunogenic compositions contain a total volume of the immunogenic composition from 5 microliters to 400 microliters.

2. The immunogenic composition according to claim 1, wherein the prime dose and boost dose each contain the same antigen(s).

3. The immunogenic composition according to claim 1, wherein the second and third immunogenic compositions formulated for intranasal administration contain an adjuvant.

4. The immunogenic composition according to claim 1, wherein the second and third immunogenic compositions formulated for intranasal administration contain one or more of:
   i) a monoester of glycerol with a fatty acid,
   ii) a fatty acid,
   iii) a combination of fatty acids, or
   iv) a mixture thereof.

5. The immunogenic composition according to claim 4, wherein the composition contains a monoester of glycerol with a fatty acid in a concentration of from 5 to 40 mg/ml.

6. The immunogenic composition according to claim 4, wherein the composition contains a fatty acid or a combination of fatty acids in a total concentration of from 2 to 40 mg/ml.

7. The immunogenic composition according to claim 1, wherein the second and third immunogenic compositions formulated for intranasal administration contain:
   i) a monoester of glycerol with a fatty ester, and
   ii) a fatty acid.

8. The immunogenic composition according to claim 1, wherein the second and third immunogenic compositions formulated for intranasal administration contain:
   i) glycerol monooleate, and
   ii) oleic acid.

9. The immunogenic composition according to claim 8, wherein the concentration of glycerol monooleate is from 2.5 to 20 mg/ml and the concentration of oleic acid is from 2.5 to 20 mg/ml in the composition.

10. The immunogenic composition according to claim 1, wherein the second and third immunogenic compositions formulated for intranasal administration are given by self-administration.

11. The immunogenic composition according to claim 1, wherein the volume of the second and third immunogenic compositions formulated for intranasal administration in each container is from about 50 µl to about 250 µl.

12. The immunogenic composition according to claim 1, wherein each container containing the second and third immunogenic compositions formulated for intranasal administration contain 50% or 100% of a vaccination dose.

13. An immunogenic composition comprising:
   a) a prime dose comprising a first immunogenic composition formulated for parenteral administration and a second immunogenic composition formulated for intranasal administration, wherein the first immunogenic composition formulated for parenteral administration and the second immunogenic composition formulated for intranasal administration contain one or more antigens from inactivated whole influenza A, influenza B or parts thereof, and
   b) a boost dose comprising a third immunogenic composition formulated for intranasal administration, wherein said third immunogenic composition formulated for intranasal administration contains one or more antigens from inactivated whole influenza A, influenza B or parts thereof.

* * * * *